(12) United States Patent
Von Drasek et al.

(10) Patent No.: US 7,005,645 B2
(45) Date of Patent: Feb. 28, 2006

(54) APPARATUS AND METHODS FOR LAUNCHING AND RECEIVING A BROAD WAVELENGTH RANGE SOURCE

(75) Inventors: William A. Von Drasek, Oak Forest, IL (US); David Sonnenfroh, North Andover, MA (US); Mark G. Allen, Boston, MA (US); Joy Stafford-Evans, Andover, MA (US)

(73) Assignees: Air Liquide America L.P., Houston, TX (US); Physical Sciences, Inc., Andover, MA (US)

( * ) Notice: Subject to any disclaimer, the term of this patent is extended or adjusted under 35 U.S.C. 154(b) by 270 days.

(21) Appl. No.: 10/294,061

(22) Filed: Nov. 14, 2002

(65) Prior Publication Data

US 2003/0152307 A1     Aug. 14, 2003

Related U.S. Application Data

(60) Provisional application No. 60/334,273, filed on Nov. 30, 2001.

(51) Int. Cl.
*G02B 6/00* (2006.01)

(52) U.S. Cl. .............................. 250/339.13; 250/341.2; 250/343

(58) Field of Classification Search ........... 250/339.13, 250/341.2, 341.7, 343
See application file for complete search history.

(56) References Cited

U.S. PATENT DOCUMENTS

| 4,489,239 A | * | 12/1984 | Grant et al. | ........... 250/339.03 |
| 5,021,662 A | | 6/1991 | Johnson | |
| 5,047,639 A | * | 9/1991 | Wong | ...................... 250/341.1 |
| 5,170,056 A | * | 12/1992 | Berard et al. | ............ 250/341.2 |
| 5,832,842 A | | 11/1998 | Frontini et al. | |
| 6,107,631 A | * | 8/2000 | He | .......................... 250/339.09 |
| 6,636,316 B1 | * | 10/2003 | Matsumoto et al. | ........ 356/437 |

FOREIGN PATENT DOCUMENTS

| GB | 2264170 A | 8/1993 |
| WO | WO 9408226 A | 4/1994 |
| WO | WO 0133200 A | 5/2001 |

OTHER PUBLICATIONS

Allen MG: "Diode Laser Absorption Sensors For Gas-Dynamic and Combustion Flows" Measurement Science and technology, IOP Publishing Bristol, GB vol. 9, No. 4, Apr. 1, 1998, pp. 545-562, XP000780563, ISSN:0957-0233, p. 550, p. 522, and figure 2.

Ebert et al.: "Simulataneous Diode-Laser-Based in Situ Deteection of Multiple Species and Temperature in a Gas-Fired Power Plant" Proceedings of the 28$^{th}$ Symposium (International) on Combustion 2000, pp. 423-430, XP001148198, pp. 424, 426, and figure 2.

Thomson et al., : "Laser Based Optical Measurements of Electric Arc Furnace Off-Gas for Pollution Control and Energy Efficiency," Innovative Technolgies for Steel and Other Materials, Met. Soc., The Conference of Metallurgists, Toronto, Aug. 2000).

(Continued)

*Primary Examiner*—Constantine Hannaher
*Assistant Examiner*—Faye Polyzos
(74) *Attorney, Agent, or Firm*—Christopher J. Cronin

(57) ABSTRACT

An apparatus and method for simultaneous detection of N gas species through laser radiation attenuation techniques is disclosed. Each of the N species has a spectral absorption band. N laser sources operate at a wavelength $\lambda_N$ in a spectral absorption band separated by the cutoff wavelength for single-mode transmission. Each laser source corresponds to a gas species and transmits radiation through an optical fiber constructed and arranged to provide single-mode transmission with minimal power loss.

34 Claims, 9 Drawing Sheets

OTHER PUBLICATIONS

Furlong, et al., : "Diode-Laser Sensors for Real Time Control of Temperature and H2O in Pulsed Combustion Systems," 34th AIAA/ASME/SAE/ASEE Joint Propulsion Conference, AIAA-98-3949, 1998.

Ebert, V. et al. :"Simulataneous Laser Based in Situ Detection of Oxygen and Water in a Waste Incinerator for Active Combustion Control Purposes," Proceedings of the Twenty-Seventh Symposium (International) on Combustion, The Combustion Institute, vol. 27, pp. 1301-1308, 1998.

Von Drasek, W., et al. :"Multi-Functional Industrial Combustion Process Monitoring with Tunable Diode Lasers", Proceedings of SPIE, vol. 4201, 2000.

* cited by examiner

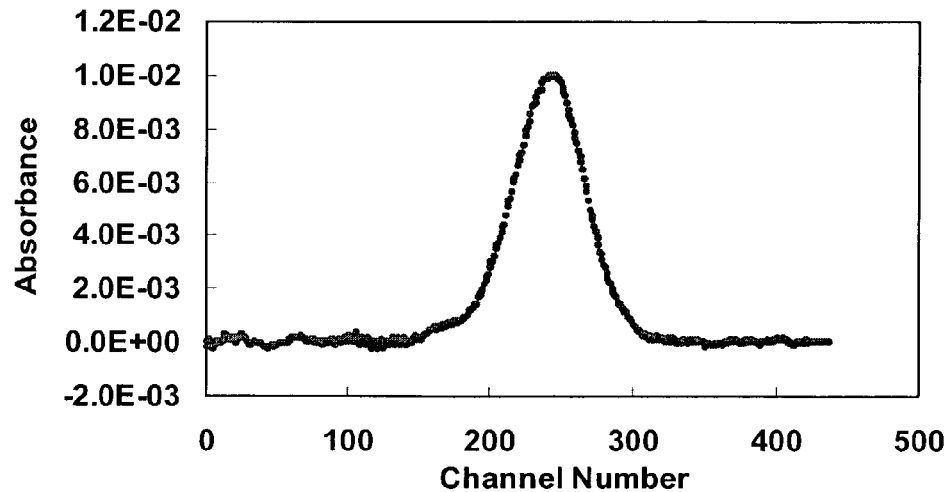
Figure 9. $O_2$ spectrum collected on a 30 MW industrial furnace wit a 48 ft. pathlength. Temperature = 1547 K determined from $H_2O$ spectrum in Figure 2 giving an $O_2$ concentration of 5.95%.
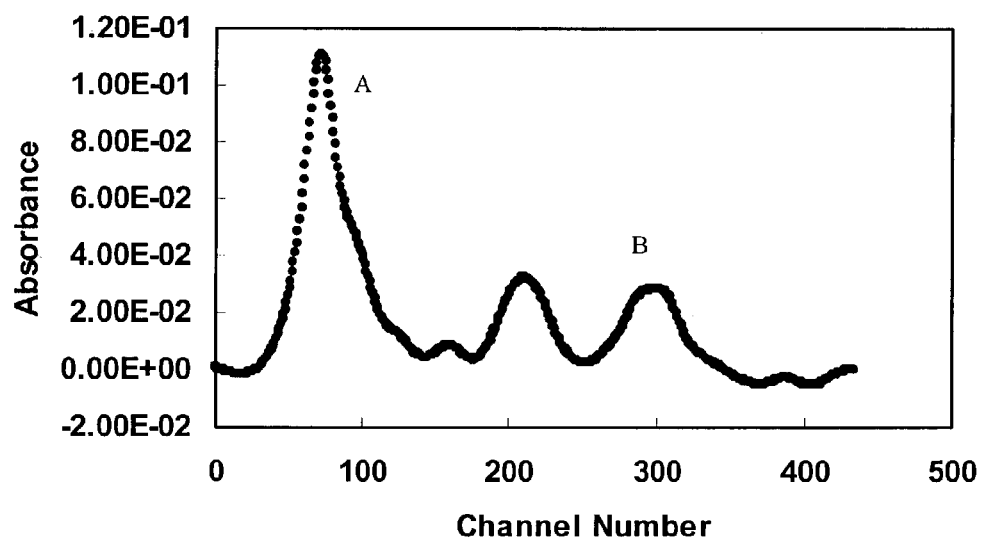
Figure 10. $H_2O$ spectrum collected on a 30 MW industrial furnace with a 48 ft pathlength. Temperature =1547 K and $H_2O$ concentration is 7.58%.

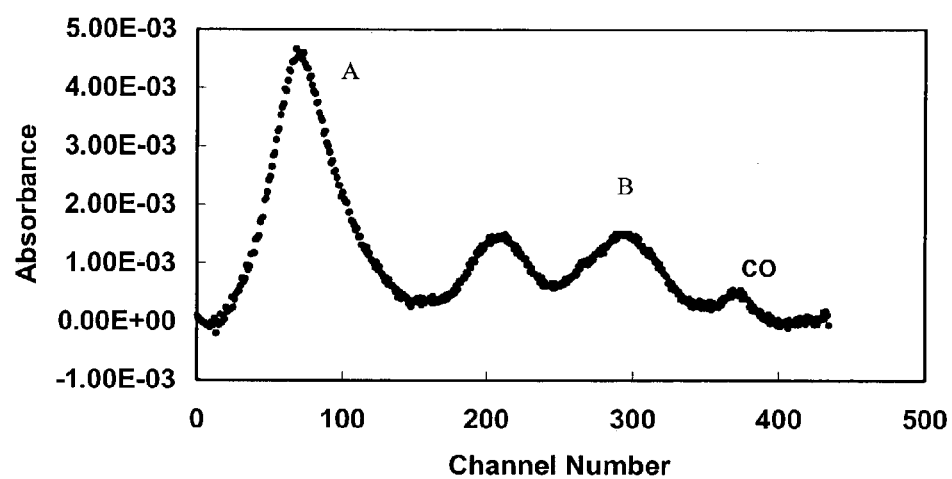
Figure 11 H$_2$O and CO spectrum collected on a 500 kW pilot furnace with a 1 ft pathlength. Temperature = 1387 K with a CO concentration of 4.7%.

APPARATUS AND METHODS FOR LAUNCHING AND RECEIVING A BROAD WAVELENGTH RANGE SOURCE

CROSS-REFERENCE TO RELATED APPLICATIONS

This application is related to abandoned application Ser. No. 09/433,667, filed Nov. 4, 1999, and to application Ser. No. 09/522,915, filed Mar. 10, 2000 and Ser. No. 60/334,273, filed Nov. 30, 2001, all of which are incorporated herein by reference. This application claims the benefit of U.S. Provisional Application No. 60/334,273, filed Nov. 30, 2001.

STATEMENT REGARDING FEDERALLY FUNDED RESEARCH

The United States Government has a paid-up license in this invention and the right in limited circumstances to require the patent owner to license others on reasonable terms as provided for by the terms of Prime Contract no. DE-FC02-00CH11030 award by the Department of Energy.

BACKGROUND OF THE INVENTION

1. Brief Description of the Invention

This invention relates generally to apparatus and methods for monitoring and/or control of industrial processes using diode laser-based sensors, in particular monitoring and/or control of combustion processes.

2. Related Art

Monitoring and control of combustion processes requires the use of sensors to provide information on gas species composition and temperature. Information on the combustion state of the process from the sensor can be assessed either by an operator or by automated process control system to determine the necessary operating parameter adjustments needed. Effective control of the process parameters provides an optimization scheme that can impact the energy efficiency, product quality, production rate, and pollutant reduction.

For combustion processes operating with hydrocarbon fuels, knowledge of the $O_2$ and CO concentration is essential to determine whether the combustion space is reducing or oxidizing. Typically, combustion space monitoring is conducted either by using extractive sampling probes or by in-situ probes. Extractive sampling uses water or gas cooled probe inserted into the process stream. The sample is extracted by drawing the process gas through the probe using a pump followed by a chiller system to remove the water vapor before reaching the gas analyzer. This technology suffers from probe and sample line plugging and other maintenance issues such as corrosion when applied to harsh process environments as encountered in glass melting tanks, steel processing furnaces, chemical processing systems, etc. In addition to maintenance issues, long sampling lines reaching up to several hundred feet are not uncommon resulting in sampling delay times that can range form seconds to several minutes. For control and optimization on dynamic processes (time varying $O_2$ and CO concentration) such as electric arc furnaces or secondary aluminum melters, a real-time measure of the combustion state is needed to adequately control the process. Sensor systems that introduce long delay times reduce the controllability and observability of the system.

In-situ monitoring of the combustion space reduces the effect of delay time; however, true in-situ probes for monitoring both $O_2$ and CO are not commercially available. Instead hybrid in-situ systems are used such as AMETEK model WDG-HPII that continuously extracts the gas sample to the analyzer mounted on the process. This system analyzes the $O_2$ concentration with a zirconium oxide probe and the combustibles (CO, $H_2$, $C_xH_y$) with a catalytic detector before returning the gas stream back to the process. Despite the elimination of the sampling line, response times are still on the order of 10's of seconds and maintenance issues persist on high particle density applications, since the gas is drawn through the instrument.

The drawbacks associated with conventional monitoring technologies can be avoided by using non-intrusive optical techniques based on measuring absorbed radiation from a source that propagates through a medium. In particular, the emergence of tunable diode lasers in the near-infrared provide a source of radiation that can access absorption transitions of important chemical species such as CO, $O_2$, $H_2O$, $CO_2$, etc. providing an alternative analytical measurement technique that has been demonstrated in both laboratory and industrial settings. The measurement is conducted by launching a beam of radiation across the process to a receiver that monitors the modulated radiation intensity. By ramping the injection current to the device the laser can be rapidly tuned across a resonance absorption transition of the targeted specie to record an absorption spectrum that contains both the baseline and the absorption line feature. The Beer-Lambert relation describes the resulting absorption of the laser radiation along the measurement path for a single species given by $$I_v = I_{v,o} e^{[-S(T)g(v-v_o)Nl]} \quad (1)$$

where $I_v$ is the laser intensity at frequency v measured after the beam has propagated across a path l with N absorbing molecules per volume. The incident laser intensity is $I_{v,o}$ and is referred to as the reference. The amount of laser radiation attenuated is determined by the temperature dependent linestrength S(T) and the lineshape function $g(v-v_o)$. Inversion of Eq. 1 relates the number density N to the measured laser intensities and known linestrength and pathlength given by $$N = \frac{1}{S(T)l} \int \ln\left(\frac{I_{vo}}{I_v}\right) dv \quad (2)$$

The rapid tunability of the diode laser (reported values up to 1000 Hz by Allen, M. G., "Diode Laser Absorption Sensors for Gas-Dynamic and Combustion Flows", *Measurement Science and Technology*, Vol. 9, pg. 545–562, 1998) allows signal averaging of several hundreds of spectra over a short time interval (<1 sec). The fast time response of the technique provides essentially real-time process monitoring suitable for dynamic monitoring and control.

In monitoring applications on industrial processes, multiple species or multiple absorption line detection is often required to obtain sufficient information on the state of the process for monitoring and control purposes. However, the current tuning range for standard diode lasers, for example, distributed feedback or vertical cavity surface emitting lasers (VCSEL's), are limited to only ~1–3 $cm^{-1}$. Therefore, in only few selected examples can multiple species (or absorption lines) be monitored using a single laser. For example, Thomson et al. ("Laser Based Optical Measurements of Electric Arc Furnace Off-Gas For Pollution Control and Energy Efficiency", Innovative Technologies for Steel and Other Materials, Met Soc., The Conference of Metallurgists, Toronto, August 2000) demonstrated CO and $H_2O$ monitoring at 1577.96 and 1578.1 nm, respectively, using a single diode laser and jump scan technique to monitor both species.

To expand the number of monitored species, systems have been designed utilizing fiber optic components to integrate multiple lasers together. The compatibility of near-infrared ("NIR") lasers with fiber optic components provides a means to multiplex systems together using several diode lasers to access the targeted wavelength regions. A demonstration of the multiplexing capability is shown by Furlong et al., "Diode-Laser Sensors for Real-Time Control of Temperature and $H_2O$ in Pulsed Combustion Systems," 34th *AIAA/ASME/SAE/ASEE Joint Propulsion Conference*, AIAA-98-3949, 1998, where multiple $H_2O$ absorption lines are monitored using two lasers at 1.392 and 1.343 $\mu$m. Here fiber optic couplers were used to combine the output of each laser into a single fiber to transport the radiation to the process. The ability to launch the radiation across the process from a single fiber minimizes optical access requirements and reduces the complexity of the optical system. However, at the receiver side, the beam is composed of multiple wavelengths that must be demultiplexed using dispersive elements to separate the radiation and direct it to individual detectors. Alternatively, time domain multiplexing can be used, where the laser scans are conducted at different phases providing near simultaneous detection of the species at the receiver. (Allen, M. "Diode laser absorption sensors for gas-dynamics and combustion flows", Meas. Sci. Technol. 9 (1998) pp. 545–562.) Regardless of the means used, multiplexing into a single fiber with the criteria of maintaining single-mode transmission, minimum energy loses, and insensitivity to mechanical stress such as bending and vibration requires that the input wavelengths are reasonably close. The constraint placed on utilizing a single fiber for transporting multiple wavelengths while maintaining single mode transmission is described by $$D < \frac{2.4\lambda}{\pi\sqrt{n_o^2 - n_1^2}} \tag{3}$$

where D is the maximum core fiber diameter, $\lambda$ is the wavelength, $n_0$ is the refractive index of the fiber core and $n_1$ is the refractive index of the fiber cladding. If the core diameter, D, is larger than the right hand side ("RHS") of the inequality, then the fiber can carry multiple modes. Rearranging equation 3 to solve for $\lambda$ defines the cutoff wavelength, i.e., for single mode transmission, the wavelength must be greater than the cutoff wavelength for a given set of fiber parameters.

For combustion monitoring applications to monitor and/or control the degree of reducing or oxidizing atmosphere, the important combustion species are CO and $O_2$. In the near infrared CO absorption is described by the second overtone (3,0) band near 1560 nm whereas $O_2$ absorption is monitored from the b-X (0,0) band near 760 nm. In this case, the large difference in wavelengths prohibits combining the output of each laser into a single fiber while minimizing energy loses and maintaining single-mode transmission. To maintain single-mode transmission, a fiber diameter of 5 $\mu$m is required for 760 nm and 9 $\mu$m for 1560 nm.

In addition to fiber incompatibility over the broad wavelength range, any transparent optics used in the system such as beam expanders, collimators, focusing lenses, windows, and the like, preferably have an antireflective coating to minimize reflections propagating through the optical train. Without suppressing the resulting reflections from the optical surfaces, interference fringe patterns (etalons) on the recorded absorbance spectrum are produced, thus degrading the quality of the measurement. In the case of $O_2$ and CO detection an antireflective coating functioning over the broad wavelength range spanning 800 nm is required. The maximum off-the-shelf broadband antireflective coating available can approach ~500 nm in the NIR over the range of 1050–1600 nm, which is not sufficient for use in an $O_2$ and CO monitoring application. Instead a double vee antireflective ("AR") coating that has a minimum reflectivity over a narrow bandwidth at 760 and 1560 nm can be used. The wavelength dependence on AR coated optics and fiber optic diameter constraints have led to previous multiple species detection schemes to use separate optical access for monitoring CO and $O_2$, as disclosed by Frontini et al. of Finmeccanica S.p.A. (U.S. Pat. No. 5,832,842) where a single laser plus detector system is used per species requiring multiple line-of-sight access points on the process. Similarly, commercially available diode laser systems for monitoring $O_2$ and CO are presently manufactured by Norsk Electroptics (Norway) and Altoptronic (Sweden). However, in both cases each species is monitored using a dedicated beam launch and receiver unit for each species. Multiple species monitoring would require not only additional dedicated systems, but also additional line-of-sight optical access ports on the process. This approach is both costly and cumbersome, limiting the application to only cases where the additional cost can be justified. It is therefore desirable to interface the optical system to the process with minimum components and minimum optical access points.

A demonstration of the integration of a broad range of wavelengths into a single system was shown by Ebert et al. for $O_2$ (760 nm), $H_2O$ (812 nm), and $CH_4$ (1650 nm) monitoring on a 1 GW powerplant (Ebert, V., et al., "Simultaneous Diode Laser-Based In situ Detection of Multiple Species and Temperature in Gas-Fired Power Plant", *Proceedings of the Twenty-Eighth Symposium (International) on Combustion, The Combustion Institute*, Vol. 28, pp. 423–430, 2000) and $O_2$ (760 nm) and $H_2O$ (812 nm) monitoring on a 20 MW waste incinerator (Ebert, V., et al., "Simultaneous Laser-based In situ Detection of Oxygen and Water in a Waste Incinerator For Active Combustion Control Purposes", *Proceedings of the Twenty-Seventh Symposium (International) on Combustion, The Combustion Institute*, Vol. 27, pp. 1301–1308, 1998). In this case, all lasers were mounted close to the process with associated optics for collimating and overlapping the beams. On the receiver side, the multiple wavelength-transmitted beam was separated onto multiple detectors using narrowband interference filters and focusing mirrors. In this case, the measurements were conducted by direct absorption using lasers that were not fiber optically coupled, thus having a specific polarization allowing the use of non-anti-reflective coated Brewster angled windows. Though the system incorporates a broad wavelength range, issues related to placement of the sensitive lasers and associated electronics near the harsh combustion process and the complexity of the optical arrangement to collimate and combine the beams are significant drawbacks. For industrial applications, the lack of robustness is not acceptable for continues day-to-day operation.

SUMMARY OF THE INVENTION

In accordance with the present invention, launch and receiver designs are described that address the drawbacks outlined above. The innovative designs are adaptable to broad wavelength range sources with minimum number of optical components. The simplicity of the designs enhances overall robustness of the optical beam transport, which is advantageous in industrial applications. The designs presented here are preferably can be divided into separate categories; launch and receiver; and near and far field. A complete description is presented herein.

A first aspect of the invention is apparatus for simultaneous detection of X gas species through laser radiation attenuation techniques where the distance between a beam launch module and a receiver module is sufficiently short, preferably not more than about 30 centimeters, to permit capturing of the multiple wavelength beams at the receiver, each of the X species having a near-infrared spectral absorption band separated by at least 500 nanometers from each other, the apparatus comprising:
- (a) N laser sources, wherein each of the N laser sources is adapted to operate at a wavelength $\lambda_N$ in a near-infrared spectral absorption band separated by at least 500 nanometers from each other, and each laser source corresponding to a gas species;
- (b) each of the N laser sources adapted to transmit radiation through an optical fiber (preferably dedicated), each optical fiber having single-mode optical fiber characteristics sufficient to insure single-mode transmission with minimal power loss to a beam splitter, said beam splitter sending a first portion of each of the N laser's radiation to a balanced ratiometric detector, and a second portion to a compound ferrule;
- (c) the compound ferrule designed so that each single-mode optical fiber terminating therein is held at a separation distance which is small relative to a focal length of a collimating optical component (preferably an off-axis parabolic or an achromate lens) to which the N beams are directed by the compound ferrule, the collimating optical component adapted to route N collimated laser beams through a process containing N gas species to be detected;
- (d) means for receiving and detecting nonabsorbed radiation from each laser and creating N outputs for each laser wavelength $\lambda_N$; and
- (e) means for routing the N outputs to the balanced ratiometric detector.

Preferred apparatus are those wherein each of the N laser sources transmits through a dedicated corresponding single-mode optical fiber to the compound ferrule, and apparatus wherein the compound ferrule is positioned within the beam launch module. Yet other preferred apparatus are those wherein the means for collimating is an off-axis parabolic mirror; apparatus comprising a multi-chromic mirror having reflectance only for narrow bandpasses around the $\lambda_N$ wavelengths, the multi-chromic mirror directing nonabsorbed radiation onto a second off-axis parabolic mirror, then through an iris, and then to an enhanced short wavelength InGaAs photodetector, the photodetector producing an output for each $\lambda_N$ wavelength that is sent to the balanced ratiometric detector. Still other preferred apparatus are those wherein the balanced ratiometric detector produces an output that is digitized and analyzed by a means for data acquisition; apparatus wherein the $\lambda_N$ laser wavelengths are launched such that each beam is spatially separated from the other beams; and apparatus wherein the gas being measured is bound by inlet and outlet windows coated on a portion thereof with antireflection coatings specific to each of the $\lambda_N$ wavelengths. Preferably, the receiving module includes N mirrors each having a narrow bandpass reflectance specific to each $\lambda_N$ wavelength and letting all other wavelengths pass through, and preferably each N mirror has a corresponding off-axis parabolic mirror, an iris, and a detector, each detector optically connected to the balance ratiometric detector. In other preferred embodiments, the off-axis parabolic mirror directs the N beams through the process and hence onto a grating, and each N mirror has a corresponding off-axis parabolic mirror, an iris, and a detector, each detector optically connected to the balance ratiometric detector. Preferably, the beams from the grating are reflected by and forwarded by N spherical mirrors, to respective iris and detectors, and then to the balanced ratiometric detector.

A second aspect of the invention is a method for simultaneous detection of N gas species through laser radiation attenuation techniques where the distance between a beam launch module and a receiver module is short (preferably not more than 30 centimeters), each of the N gas species having a near-infrared spectral absorption band separated by at least 500 nanometers from each other, the method comprising:
- (a) launching N laser wavelengths from N laser sources, wherein each of the N laser sources operates at a wavelength $\lambda_N$ in a near-infrared spectral absorption band, each wavelength $\lambda_N$ separated by at least 500 nanometers from each other, and each laser source corresponds to a gas species;
- (b) transmitting radiation from each of the N laser sources through an optical fiber (preferably dedicated), each optical fiber having single-mode optical fiber characteristics sufficient to insure single-mode transmission with minimal power loss to a beam splitter, the beam splitter sending a first portion of each of the N laser's radiation to a balanced ratiometric detector, and a second portion to a compound ferrule;
- (c) separating each single-mode optical fiber using the compound ferrule at a separation distance which is relatively short, preferably less than 10 percent and perhaps even less than 1 percent of the focal length of a collimating optical component (preferably selected from the group consisting of an of-axis parabolic and an achromate lens) to which the N laser beams are directed by the compound ferrule, thus creating N collimated laser beams;
- (d) routing the N collimated laser beams through a process having N species to be detected; and
- (e) receiving and detecting nonabsorbed radiation corresponding to the N gas species.

Preferred methods are those wherein each of the N laser sources transmits through a dedicated corresponding single-mode optical fiber to the compound ferrule, and the compound ferrule is positioned within the beam launch module. Yet other preferred methods are those wherein the means for collimating is an off-axis parabolic mirror; methods further employing a multi-chromic mirror having reflectance only for narrow bandpasses around the $\lambda_N$ wavelengths, the multi-chromic mirror directing nonabsorbed radiation onto a second off-axis parabolic mirror, then through an iris, and then to an enhanced short wavelength InGaAs photodetector, the photodetector producing an output for each $\lambda_N$ wavelength that is sent to the balanced ratiometric detector. Yet other preferred methods are those wherein the balanced ratiometric detector produces an output, and that output is digitized and analyzed by a means for data acquisition. Preferably, the N laser beams are launched such that each beam is spatially separated from the other beams, and the beams are routed through the gas being measured which is bound by inlet and outlet windows coated on a portion thereof with antireflection coatings specific to each of the $\lambda_N$ wavelengths. Preferably, the beams are then routed to a receiving module that includes N mirrors each having a narrow bandpass reflectance specific to each $\lambda_N$ wavelength, the mirrors letting all other wavelengths pass through. Preferably, each of said N mirrors routes a beam to a corresponding off-axis parabolic mirror, an iris, and a detector, each detector optically connected to the balanced ratiometric detector. In some preferred embodiments, the off-axis parabolic mirror directs the N beams through the gas and hence onto a grating, each N mirror having a corresponding off-axis parabolic mirror, an iris, and a detector, each detector optically connected to the balanced ratiometric detector. Preferably, the grating reflects the N beams and forwards the reflected beams to N spherical mirrors, to respective iris and detectors, and then to the balanced ratiometric detector.

A third aspect of the invention is apparatus for simultaneous detection of N gas species through laser radiation attenuation techniques where the distance between a beam launch module and a receiver module is short (preferably not more than 30 centimeters) to capture the multiple wavelength beams at the receiver, each of the N species having a near-infrared spectral absorption band separated by at least 500 nanometers from each other, the apparatus comprising:

(a) N laser sources, wherein each of the N laser sources is adapted to operate at a wavelength $\lambda_N$ in a near-infrared spectral absorption band separated by at least 500 nanometers from each other, and each laser source corresponding to a gas species;

(b) each of the N laser sources adapted to transmit radiation through an optical fiber (preferably dedicated), each optical fiber having single-mode optical fiber characteristics sufficient to insure single-mode transmission with minimal power loss to N achromate lenses, each achromate lens having a proper wavelength-specific anti-reflective coating, the N achromate lens adapted to create N collimated laser beams;

(c) means for launching the N collimated laser beams into the process containing the N gas species to be detected (the means for launching preferably selected from the group consisting of a dichroic beam combiner or a system of mirrors); and (d) means for receiving and detecting nonabsorbed portions of the N collimated laser beams.

Preferred apparatus are those wherein the means for receiving and detecting comprises a prism and an achromate lens, and spherical lens combination that provides wavelength dispersion, beam focusing, and spatial control. The wavelength dispersion provides a means to separate the individual N wavelengths launched through the process, while focusing controls the beam spatial position relative to the detection means. Apparatus embodiments within the third aspect of the invention are less sensitive to beam steering effects that can occur due to process vibration, alignment drifting, and refractive index changes due to hot gas environments.

Further aspects and advantages of the invention will become apparent after reviewing the following non-limiting description.

BRIEF DESCRIPTION OF THE DRAWINGS

FIG. 9 is a schematic illustrating expected data for the $O_2$ spectrum.

FIG. 10 is a schematic illustrating expected data for the $H_2O$ spectrum.

FIG. 11 is a schematic illustrating expected data for the CO spectrum.

DESCRIPTION OF PREFERRED EMBODIMENTS

Figure 1:
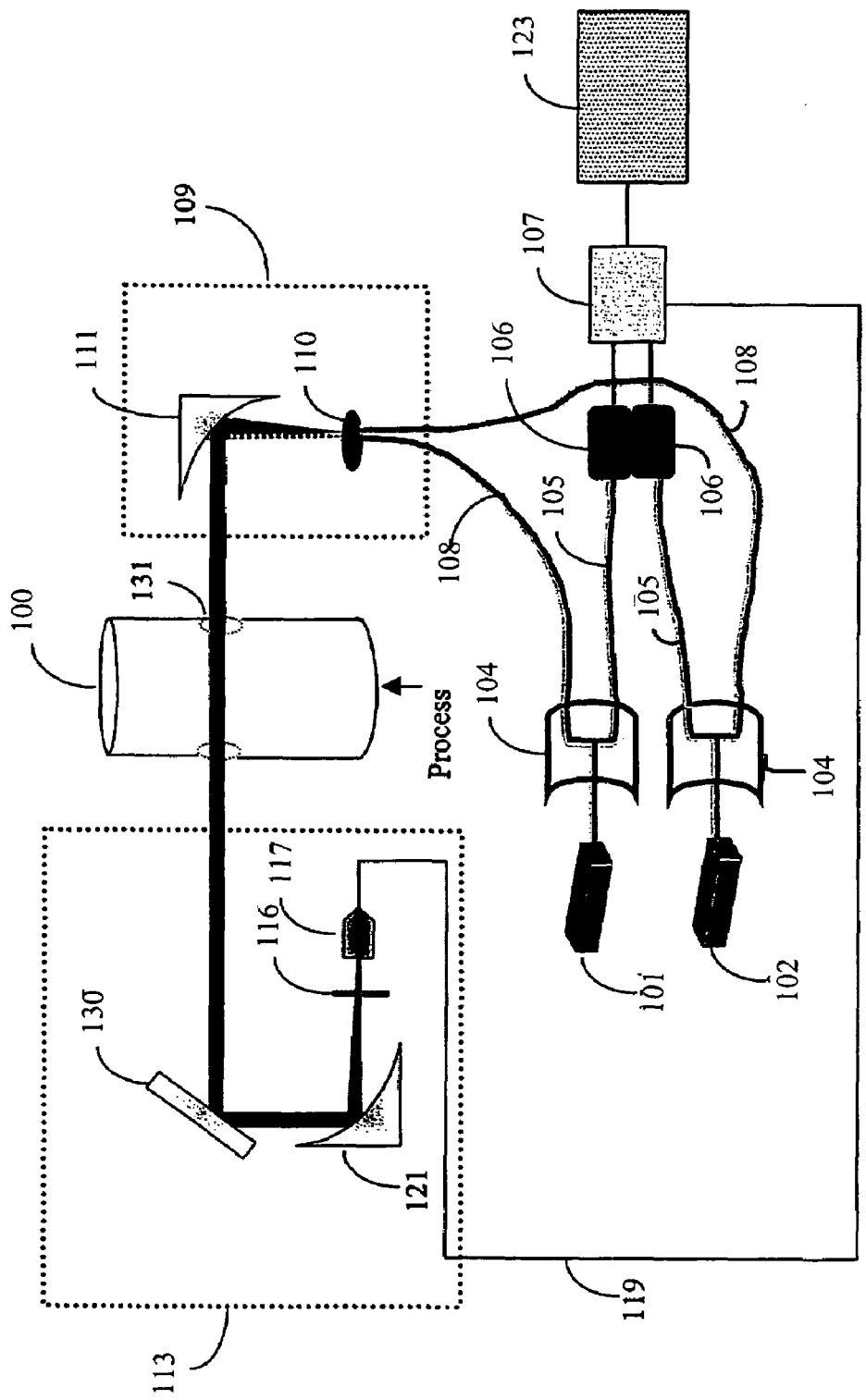
FIG. 1 is a schematic illustration of one preferred apparatus and method embodiment in accordance with the invention, illustrating launching multiple diode laser beams with collimated and expand beam diameter through a process, receiving the beams in a time domain demultiplexing mode to a single detector.

To integrate multiple wavelength lasers into a single beam launch and receiving apparatus, three key design features are used in each apparatus and method embodiment of the invention. The first key design feature addresses the issue of transporting multiple wavelengths to the launch module that is mounted on or very near the process being measured, monitored, and/or controlled. Since a single optical fiber cannot be used to transport broadly separated wavelengths, for example, wavelengths used for $O_2$ and CO monitoring, a means for launching and controlling the beam geometry is required. For cases where the distance between the launch module and receiver module is sufficiently short (say no more than 30 centimeters) a combination compound ferrule housing separate fibers for each wavelength and off-axis paraboloid mirror is one preferred means. Use of a compound ferrules allows interfacing a plurality of separate fibers that preferably have low power losses, operate at single-mode, and are insensitive to mechanical stresses, for the transport of a corresponding plurality of laser beams having respective wavelengths to a launch module. In a preferred embodiment, the compound ferrule allows interfacing a 5 micrometer ($\mu$m) diameter fiber for transporting a 760 nanometer (nm) beam in single-mode with a 9 $\mu$m diameter fiber for transporting a 1560 nm beam, also in single mode. At the end of each of the plurality of fibers, preferably no additional optics are used (except a collimating optical element), thus each single-mode beam is allowed to exit its respective optical fiber and expand with a divergence set by the wavelength-fiber combination, in other words a numerical aperture. Alternatively, in place of a compound ferrule, each single-mode optical fiber feeds an expanded beam to a respective collimating achromate lens.

The combination of a collimating optical component (for example an off-axis parabolic mirror, an achromate lens, or other beam collimating means) with wavelength-fiber pairing is a second key design feature of apparatus and methods of the invention. This combination provides the desired beam diameter, with minimum divergence. An expanded diameter beam, with the desired beam diameter, propagates through the process to be measured, monitored, and/or controlled to minimize the effect of particulate laden flow streams and refractive index gradients, as discussed in Von Drasek, W., et al., "Multi-functional Industrial Combustion Process Monitoring with Tunable Diode Lasers," Proceedings of SPIE, Vol. 4201, 2000.

Finally, use of means for reducing or eliminating secondary reflections, such as one or more off-axis parabolic mirrors, or mirrors and lenses having anti-reflective coatings, addresses a third key design feature of apparatus and methods of the invention. These components produce no secondary reflections that degrade measurement quality, and the use of off-axis parabolic mirrors both focus and collimate the beams to the desired diameter independent of the wavelength. In one preferred embodiment, collecting the plurality of beams on the receiver side with a matched second off-axis parabolic mirror directs and focuses the light onto one or more detectors. An additional discriminating optical element can be used to reject background radiation from a high temperature process. Demultiplexing of the collected signal beams are achieved either by dispersing the wavelengths to separate detectors or scanning the lasers out of phase as shown by Allen et al., supra. In another embodiment of the invention, achromate lenses as discussed herein, in combination with a prism and a spherical mirror may be used.

FIG. 1 illustrates one preferred apparatus and method of the invention. In this embodiment a dual laser system is illustrated, where a first optical fiber-coupled laser 101 preferably represents a 760 nm AlGaAs diode laser, for example those commercially available from Sarnoff Corp., Princeton, N.J., and a second fiber-coupled laser 102 preferably represents a 1560 nm InGaAsP laser, for example those commercially available from NEL America, Inc. Saddle Brook, N.J. An output of optical fiber-coupled laser 101 is fiber optically coupled to transport the radiation to a beam splitter 104, which splits the output into two beams, the split preferably ranging from about 60 to about 90 power percent into one leg, and from about 10 to about 40 power percent in a second leg (distributes from about 60 to about 90 percent of the input laser power to one optical fiber, and from about 10 to about 40 percent to the another optical fiber). In the configuration illustrated in FIG. 1 the larger power percentage beam is directed by an optical fiber 105 to a photo detector 106. A signal from photo detector 106 is processed by means for suppressing the amplitude noise inherent in semiconductor lasers, preferably a balanced ratiometric detector (BRD) circuit 107 substantially as disclosed in U.S. Pat. No. 5,134,276(IBM) which is incorporated herein by reference for its teaching of a BRD circuit; further detail on this aspect will be discussed below. The lower power percent beam is directed by an optical fiber 108 that terminates at a compound ferrule 110.

Similarly, an output of a second optical fiber-coupled laser 102 is preferably split the same percentage as first optical fiber-coupled laser 101 by a second splitter 104', with a higher power percent beam routed by an optical fiber 105' to a second photo detector 106', and a lower power percent beam routed by an optical fiber 108' that terminates at compound ferrule 110. Though the configuration for lasers 101 and 102 is substantially the same, optical fibers 105 and 108 transporting the radiation are preferably different than optical fibers 105' and 108' to maintain single-mode transmission in each set.

Compound ferrule 110 is preferably designed so that each single-mode fiber transporting their respective wavelengths are held in a mount at a separation distance at least equal to the sum of cladding layer radii of each fiber within compound ferrule 110. Since the separation distance is small (preferably ranging from about 100 to 500 $\mu$m), each laser beam preferably effectively originates from the same location, which is the effective focal position of the parabolic mirror. Further, each beam has essentially identical divergence angles as determined by the single-mode beam propagation at the respective wavelength.

The beams exit compound ferrule 110 diverging at an angle ranging from about 10° to about 25° solid angle propagating to an off-axis parabolic reflector (OAP) 111, such as that supplied by Melles Griot Photonics Components, Irvine, Calif. Preferably, the OAP is coated with a highly reflective surface coating, preferable rhodium or the like, for high reflectivity in the near-IR. This preferably results in collimated overlapping beams that are co-propagating through process 100 where the combined beams enter process 100 by optical access port 131. Compound ferrule 110 and OAP 111 are preferably housed in a hardened case 109 protecting them from the surrounding environment. Coupling of case 109 to the process is obtained by water or gas cooled pipe fixtures (not illustrated). For $O_2$ monitoring, case 109 along with the mounting fixture should be purged by a non-corrosive gas, preferably a gas having $O_2$ concentration less than 100 parts per million (ppm).

A beam receiver section is preferably housed in a hardened case 113. The beam receiver section preferably includes a high reflectivity dichroic mirror 130 to direct the 760 nm and 1560 nm beams toward a second matched OAP 121. Dichroic mirror 130 is designed to reflect only radiation at 760 and 1560 nm with 100 nm bandpass at each wavelength, thereby reducing background radiation from the hot process. The beams are preferably directed and focused by OAP 121 on an enhanced short wavelength InGaAs photo detector 117. In front of photo detector 117, an iris 116 is preferably used to further restrict the field of view on the detector, thus reducing noise contributed from the background radiation. The output from detector 117 is sent to means for suppressing amplitude noise inherent in semiconductor lasers, preferably BRD circuit 107, with the processed signal preferably digitized and analyzed by an acquisition system 123. Discrimination between the two or more wavelengths is preferably achieved by operating the system in a time-domain-multiplexed mode whereby lasers 101 and 102 are tuned out of phase.

In the description of the apparatus embodiment in FIG. 1 the preferred means for suppressing amplitude noise inherent in semiconductor lasers is a BRD circuit. The noise canceling electronic circuitry output gives the log ratio measured intensity from the detector 117 and the reference intensity from detector 106. Alternatives to the BRD approach, whose advantages are fully discussed by Allen et al., supra, and Sonnenfroh et al., supra, for suppressing amplitude noise inherent in semiconductor lasers, such as direct absorption, frequency modulation, wavelength modulation, noise subtraction, and the like may preferably be used. Independent of the noise reduction means selected, the basic concepts of beam launch and reception of the apparatus illustrated in FIG. 1 applies.

Regarding the interface to the process in FIG. 1, the line-of-sight optical access is illustrated by the hole 131. Since both the 760 and 1560 nm beams are co-propagating along the same path, a window at 131 is preferably not used, thus minimizing reflections. However, in this embodiment, there is no protection from hot process gases flowing into beam launch case 109 or receiver case 113. Purging of both cases is preferred for cooling, removing residual $O_2$, and ensuring a positive pressure exists for protection against hot process gas. Anti-reflective coated windows are commercially available from CVI Laser Corporation, Putnam, Conn., which might provide the preferred 800 nm wavelength range needed for $O_2$ and CO monitoring. As an alternative, a window placed at Brewster's angle, (56°) could be used to eliminate any reflections from its surface.

The embodiment illustrated in FIG. 1 relies on one InGaAs detector for monitoring 760 and 1560 nm radiation. Generally, InGaAs detectors response covers 850–1600 nm, but special short wave enhanced detectors are available such as the model 575L from RIFCOS Corp., Camarillo, Calif. that claims detection down to 600 nm. However, the responsivity of the detector below 800 nm is a factor of five lower than 1560 nm. Therefore the current detector technology precludes its use due to the unacceptable performance at short wavelengths and receiver designs using multiple detectors optimized for the selected wavelengths is preferred.

Figure 4:
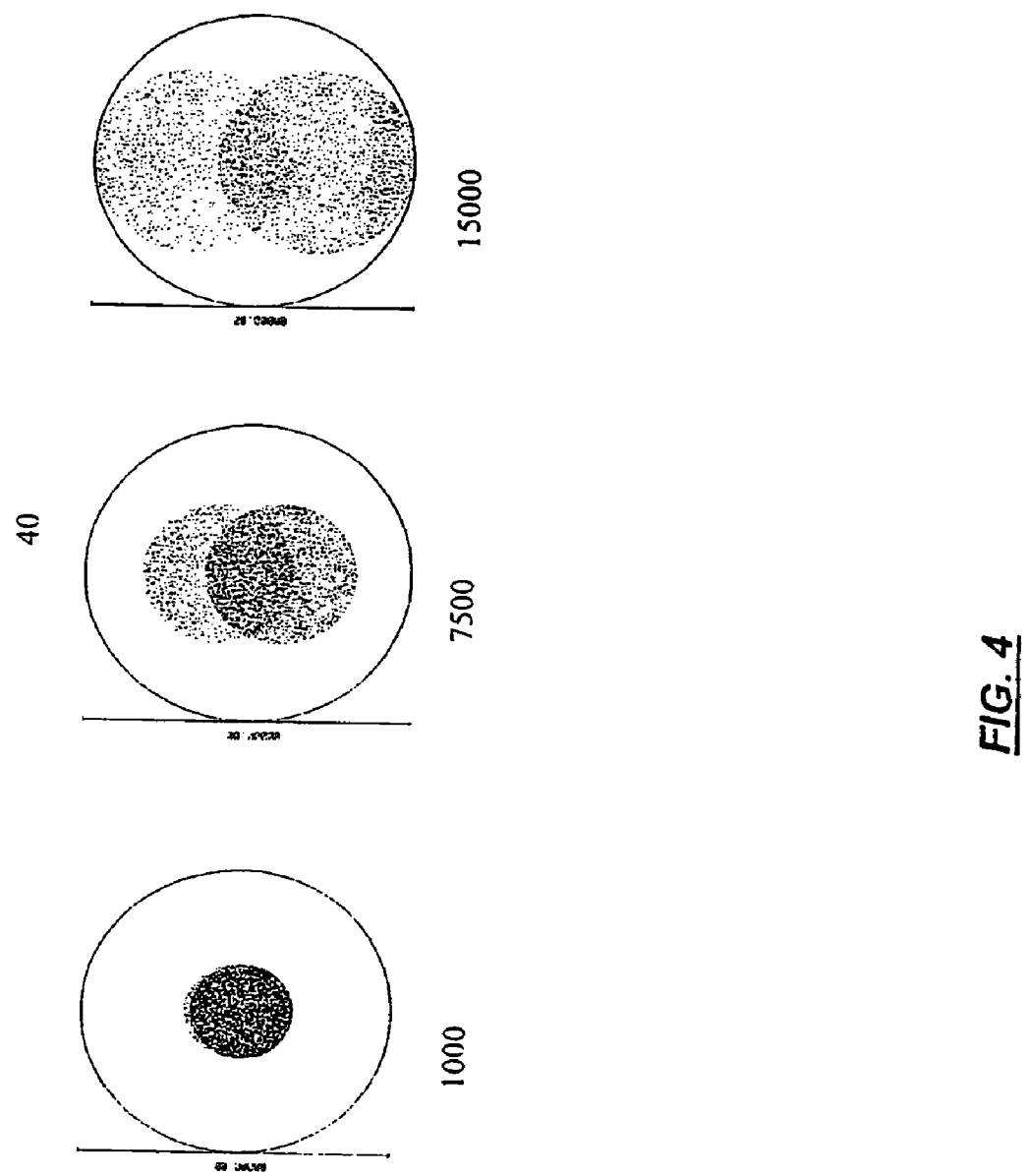
FIG. 4 is a schematic illustration of calculated spot diagrams for different distances from the launch position using the multiple diode laser beam launch methodology illustrated in FIGS. 1–3.

Characteristic calculated spot diagrams of the multiple beams launched using the apparatus of FIG. 1 (that is, a combination ferrule and OAP) are illustrated in FIG. 4 for beams at 760 and 1560 nm. These results were obtained using ray-tracing optical modeling software known under the trade designation ZEMAX from Focus Software, Inc. Tucson Ariz. The spot diagram in FIG. 4A illustrates an ideal compound ferrule with the fibers separated at 125 $\mu$m. At short distances, e.g., 1000 mm, both beams overlap and are centered within a 3 inch (7.5 cm) diameter circle. However, at larger distances 7500 and 15,000 mm the separation between the two beams increases in addition to the diameter of the beams. The diameter increase is due to divergence while the beam separation results from the separation of the two fibers mounted in the compound ferrule. The effect of beam divergence and beam separation limits the practical working distance using the combination ferrule and off-axis parabolic mirror. This limitation is due to the constraint placed on the receiver aperture. For combustion applications, where the launch and receiver modules are preferably mounted on the process, this requires line-of-sight optical access. This access is obtained by boring opposing holes through the process refractory to allow the launched beams to enter and exit the process. In general, the diameter bored in the refractory should be as small as possible to minimize heat losses from the process, minimize the exposed area of the receiver unit, and minimize the required cooling.

Because of these constraints, optical access diameters typically range from 2–4 inches (5–10 cm) and are dependent on the process. In addition, a large receiving diameter also requires large optic components to collect the beam. Optical components larger than 3 inches (7.5 cm) in diameter are both costly and have limited off-the-shelf availability. Furthermore, the selection and availability of mechanical mounts and translation stages for optical components larger in diameter than 3 inches (7.5 cm) is also limited. For these reasons, the preferred approach is to minimize the size of the receiving aperture, which in turn reduces process heat losses, reduces the required cooling, utilizes off the shelf optical components and hardware, and minimizes overall size of the receiver unit. Using the combination ferrule and off-axis parabolic mirror to launch the beam 15,000 mm through a process requires a receiving aperture greater than 3 inches (7.5 cm), as illustrated in FIG. 4, to account for alignment errors, mechanical vibration, and beam steering effects. An acceptable receiving aperture diameter to use is a factor of 2–3 times the beam diameter to allow for misalignment errors and beam steering effects.

Figure 2:
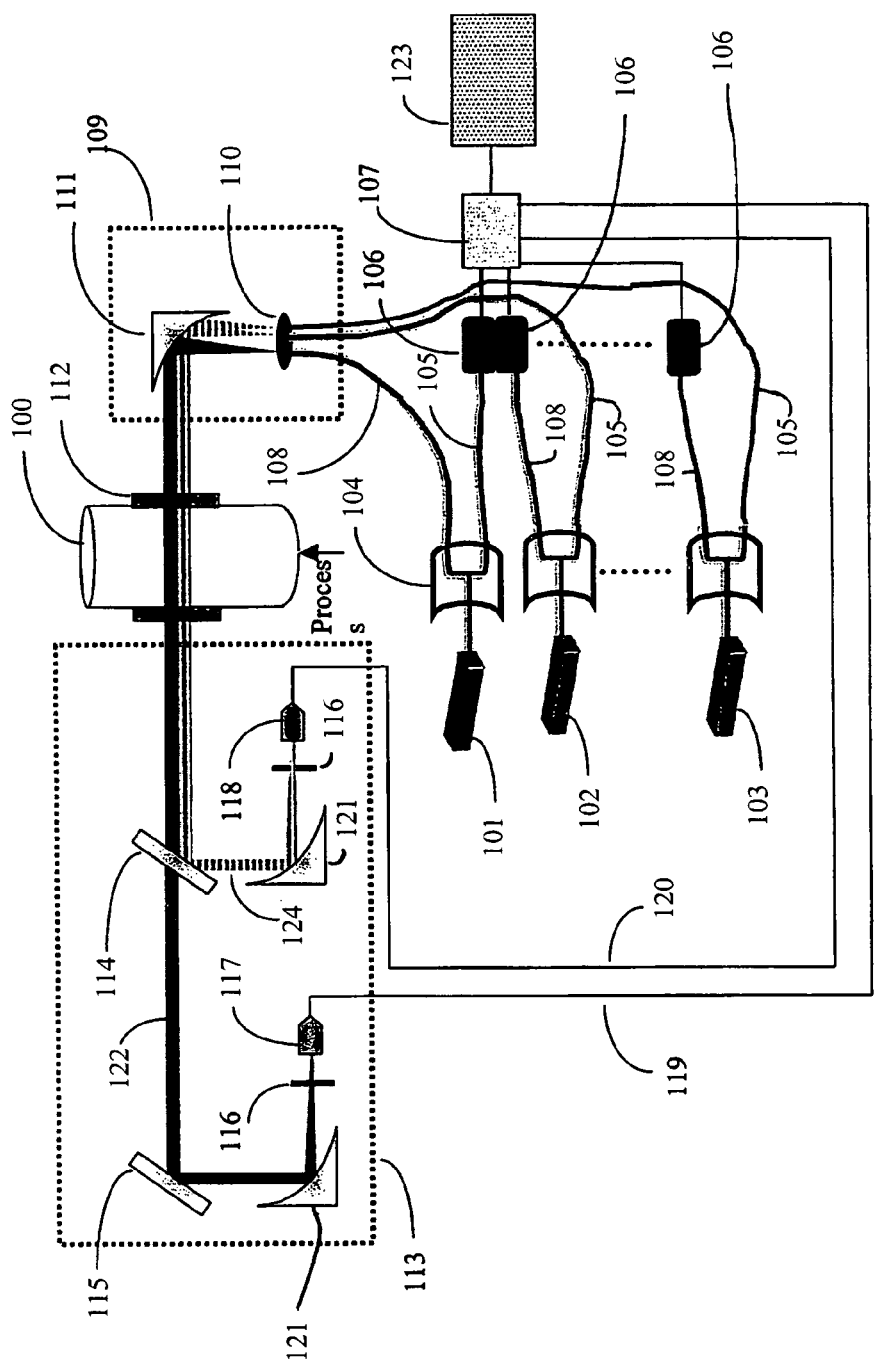
FIG. 2 is a schematic illustration of another preferred apparatus and method embodiment in accordance with the invention, illustrating launching multiple diode lasers beams with a collimated and expanded beam diameter through a process, with discrimination carried out by narrowband reflectors and reflectors/transmitters with dedicated detectors for each wavelength.
Figure 3:
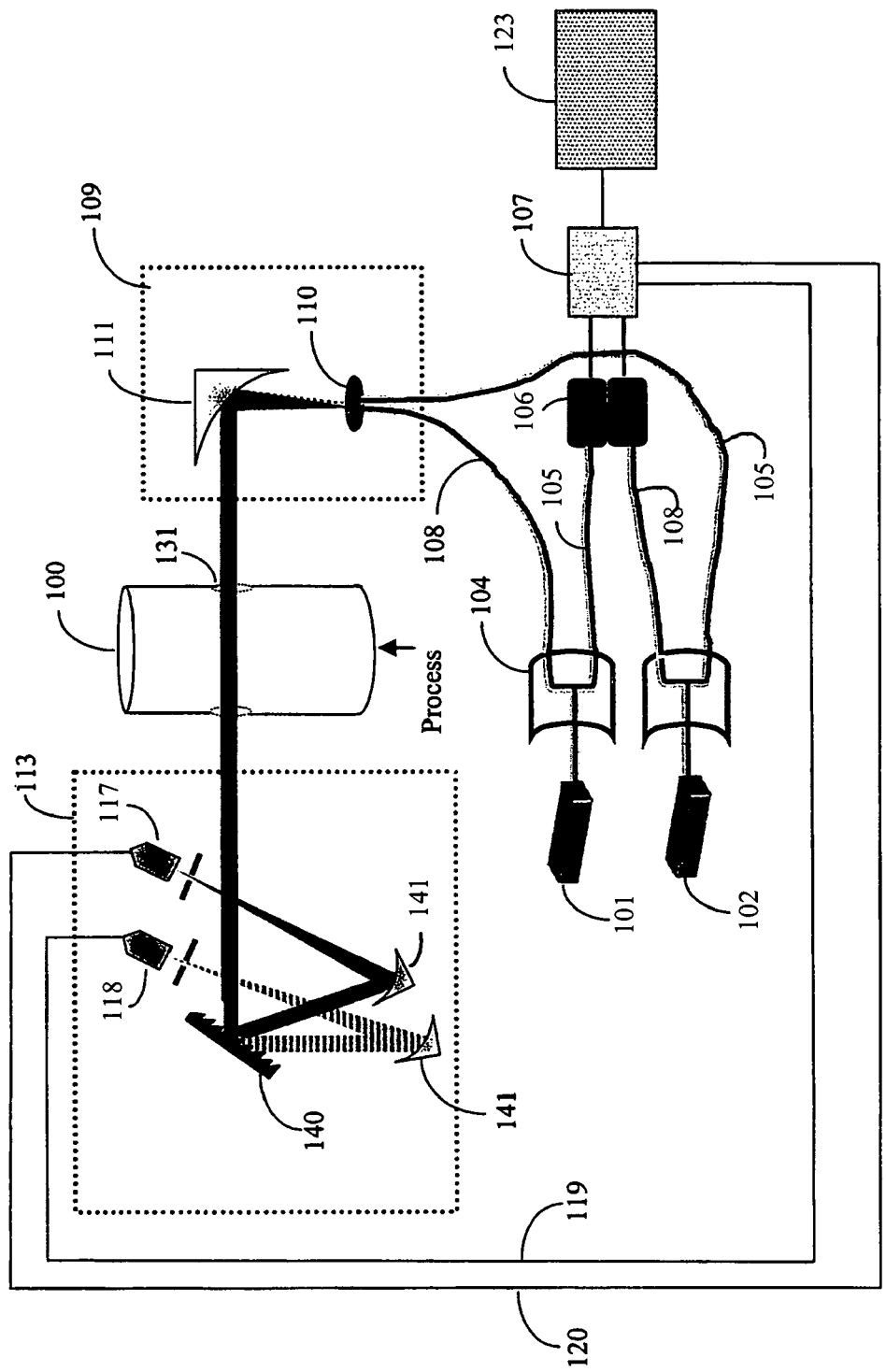
FIG. 3 is a schematic illustration of another preferred apparatus and method embodiment in accordance with the invention, illustrating launching multiple diode laser beams with a collimated and expanded beam diameter through a process with discrimination carried out by a dispersing element and dedicated detectors for each wavelength.

Two adaptations using multiple detectors are illustrated in the embodiments of FIGS. 2 and 3. In both of these configurations, the beam launch module uses an OAP 111 to collimate the beams from lasers 101, 102, and 103 traversing optical fibers 108, 108', and 108", respectively, at the desired diameter, and direct them through the process. The main differences are in the means of wavelength discrimination, and in the case of the embodiment illustrated in FIG. 2, the beams are launched such that they are spatially separated. The spatially separated beam case illustrated in FIG. 2 allows the use of anti-reflective (AR) coated windows with more standard dichroic reflectors 114 and 115. For the AR coated windows, a coating specific to 760 nm and 1560 nm are deposited on each half of the window. This is accomplished by using masking techniques in the CVD process. To achieve the desired beam separation the angle between the fibers of the compound ferrule are preferably greater than the half angle of the beam divergence to prevent beam overlapping. For the 760 and 1560 nm cases this angle is about 8°. Beam 122 propagates through the process and is transmitted through a dichroic mirror 114 and reflected by a narrowband dichroic mirror 115. The beam is then focused by an OAP 121, though an iris 116, and onto detector 117, which for the case of 760 nm radiation would preferably be a standard silicon photo detector such as is available from EG&G Optoelectronics of Gaithersburg, Md., model UV-245BQ. Similarly, beam 124 is preferably reflected by dichroic reflector 114 and focused onto detector 118 by OAP 121'. In front of both detectors, an Iris 116 and 116' are used to minimize background radiation from the process leaking through to the detector. In a preferred case of beam 124 being 1560 nm radiation, detector 118 is an lnGaAs detector such as is commercially available from Fermionics of Simi Valley, Calif., model FD3000W. Detectors 117 and 118, respectively;, generate signals which are transmitted by wire or wireless means 119 and 120, to noise reduction circuitry 107, and preferably to a digitizing and analysis system 123.

Further extension of the wavelength operating range of the system illustrated in FIG. 2 is seen by the additional laser 103 added to the that embodiment. In this case laser 103 is introduced to the beam launch module using compound ferrule 110 that preferably accepts three fibers. Alternatively, lasers 102 and 103 are preferably multiplexed using a 2×2 fiber coupler with a single fiber from the two lasers connecting to the compound ferrule. In fact, N lasers can be added to the system using a N×2 fiber coupler with the limitation being compatibility of the laser wavelengths with the fiber characteristics to insure single-mode transmission with minimal power loses. These principles apply not only to the embodiment illustrated in FIG. 2, but also to the embodiments of FIGS. 1, 3, 5 and 6.

The system illustrated in FIG. 3 is identical to the embodiment of FIG. 1 except for the receiver optics. In this embodiment, the beams are preferably introduced into the process either by the overlapping method (as in FIG. 1) or spatially separated (as in FIG. 2). In either case, the wavelength discrimination is preferably controlled using a grating 140, as illustrated in FIG. 3. Use of a planer grating requires spherical focusing elements 141 and 141' to direct and focus the separated wavelengths to the appropriate detectors 118 and 117, respectively. Alternatively, a concave holographic grating is preferably used for wavelength discrimination with the additional feature of focusing the reflected radiation onto the detector, thereby eliminating the need for elements 141 and 141' in the embodiment illustrated in FIG. 3.

Figure 6:
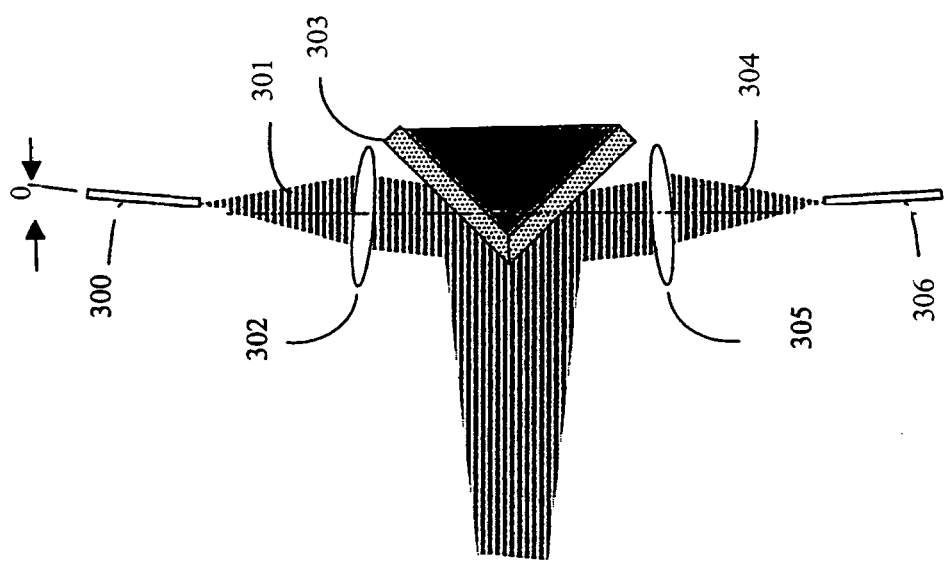
FIG. 6 is a schematic illustrating a preferred multiple wavelength beam launch apparatus and method adaptable to near or far field detection with receiving beam area minimized.
Figure 5:
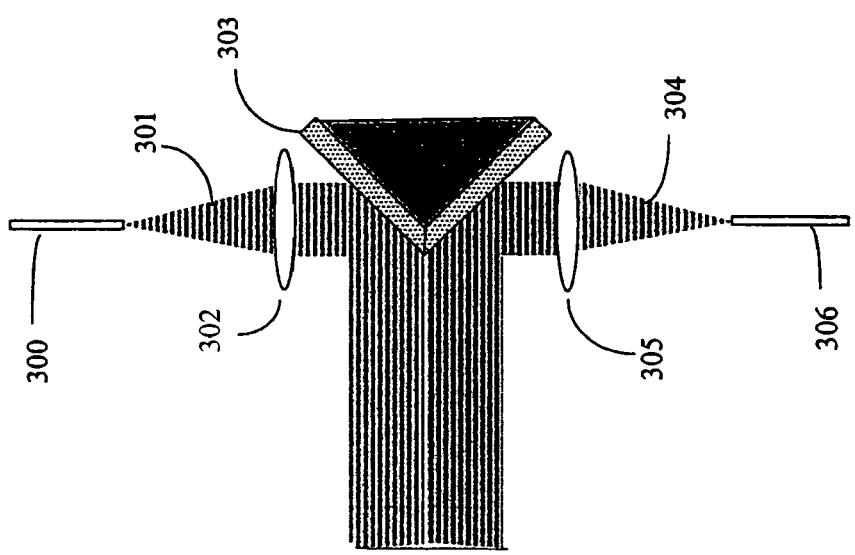
FIG. 5 is a schematic illustrating a preferred multiple wavelength beam launch apparatus and method adaptable to near or far field detection with enhanced discrimination of receiving beams.

Another preferred means to launch multiple wavelengths is to use an apparatus as illustrated in FIGS. 5 or 6. In each case separate beams are delivered to a launch module (not shown) by fibers 300 and 306, each fiber being specific to the transported wavelength to maintain minimum loses and single-mode transmission. The radiation 301 and 304 exiting fibers 300 and 306 diverges and is collimated by collimating means, such as an achromat or gradium lens 302 and 305, to avoid spherical aberration. Lenses 302 and 305 preferably have an anti-reflective coating specific to the wavelength. After collimation the beams are reflected off a mirrored prism 303 and directed into the process (not illustrated). This configuration allows the beams to propagate parallel to one another (as illustrated in FIG. 5 or by slightly angling the fiber-lens combination by an angle θ (as illustrated in FIG. 6) the beams can be set to overlap at any distance. The flexibility incorporated into the design provides the user the ability to set-up the launch with completely separated beams that can improve wavelength discrimination on the receiver side. A side-by-side beam configuration (FIG. 5) is preferred when alignment and beam steering issues are not a factor, e.g., short pathlength. For long path lengths, alignment and beam steering become important requiring higher tolerances on the receiver aperture, thus favoring an overlapped beam configuration such that the beams overlap on the receiver aperture (FIG. 6).

Figure 7:
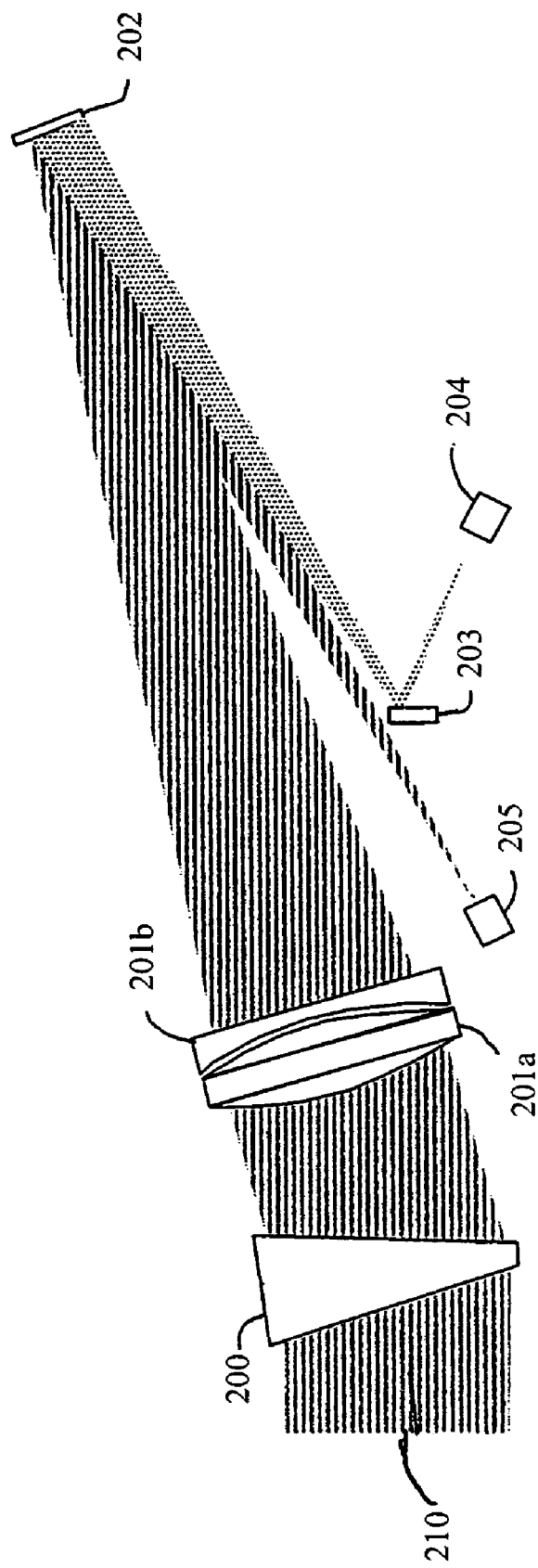
FIG. 7 is a schematic illustrating another preferred optical apparatus and method for receiving and detecting multiple wavelength radiation sources.

Preferred means to collect launched multiple wavelength beams is to use a prism-achromat lens combination, as illustrated in FIG. 7. This approach is advantageous when beam steering effects are present, caused by either refractive index gradients or mechanical movement of the receiver relative to the launch. For $O_2$ and CO monitoring, a system of the invention preferably comprises a prism 200, achromat lens comprising a convex lens 201a and a concave lens 201b, separated either by an air gap or cement, and spherical mirror 202. The combination of these three optical elements disperses multiple wavelengths received and focuses the radiation to a spatial target, e.g., detector. The incoming multiple beams can be received anywhere within the shaded area 210, which represents the same diameter as the receiving window. In practice, the combined incident spot diameter of the received beams diameter is on the order of 1 inch (2.5 cm). Therefore, a 3 inch (7.5 cm) diameter receiving window followed by the prism-achromate lens combination scaled to accept a 3 inch (7.5 cm) diameter beam provides up to 90% variation in beam position that can be caused by mechanical vibration, beam steering due to thermal gradients and/or misalignment. This figure of 90% was obtained from the formula: 100*(A1-A2)/A1 where A1 is the area of the receiver window and A2 is the area of the beam (multiple beams) incident on the window- This is only one way of expressing this point.

For prism 200 the material used should have a high refractive index to provide sufficient dispersion, e.g., a prism made with Schott Glass SFL6 results in a dispersion of 13.7 micron/nm over a distance of 450 mm from the prism. The dispersion can be increased by using either a larger prism angle or stronger convx mirror. For a larger prism, caution is needed, since the angle of the incident laser beam will also increase reducing the efficiency of the AR coating which works best at small incident angles. Using a stronger convex mirror 202 will enhance the dispersion at a longer focal position and increasing the astigmatism. For example, decreasing the focal length 20 mm (going from 270 to 250 mm) results in a dispersion of 16.2 micron/nm. The resulting larger spot sizes and astigmatism can be reduced by incorporating additional focusing elements.

Figure 8:
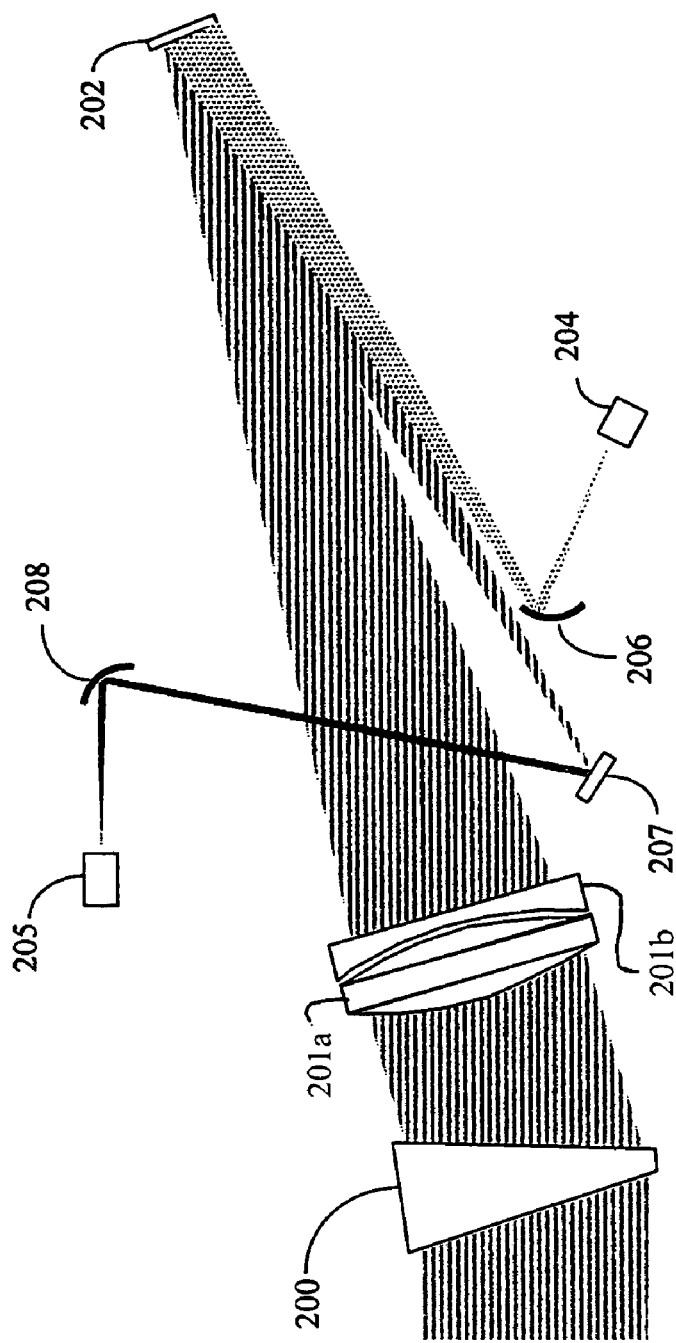
FIG. 8 is a schematic illustrating another preferred optical apparatus and method for receiving and detecting multiple wavelength radiation sources with enhanced discrimination of the dispersed beam.

After the multiple dispersed beams focus off the spherical mirror 202 the beams are focused into detector 205 which can be a Si photodiode for monitoring the 760 nm radiation used for $O_2$ absorption measurements. Since the dispersion between the two beams is relatively small for inserting standard size optical components, mirror 203 (standard flat mirror with high reflectivity for 1560 nm) can be used to divert the 1560 nm radiation used for CO and $H_2O$ monitoring to an InGaAs detector 204. Alternatively, a side-by-side detector arrangement could be implemented to element mirror 203. Adapting this configuration would just require a dual detector mount to support both detectors. In addition, an iris in front of each detector is desirable to reduce background radiation. For monitoring on high temperature processes, the background radiation level reaching the detector can be high. This is particularly problematic for monitoring $O_2$, since the incident laser power from fiber coupled AlGaAs DFB lasers is typically only a few 100 $\mu$W. In this case the background radiation can be on the same order as the laser radiation despite the dispersion by the prism configuration. FIG. 8 illustrates a mechanism to solve this problem. Here enhanced discrimination is preferred, such as by introducing a high efficiency grating 207, e.g., 830 grooves/mm blazed at 800 nm from Edmund Industrial Optics, Barrington, N.J., is illustrated in FIG. 8. The grating can be angled to reflect the $1^{st}$ order diffracted 760 nm beam across an off-axis parabolic mirror 208 to focus the beam on detector 205. For the 1560 nm radiation, a grating is not needed since the incident laser power is several milliwatts. This level of laser power is sufficiently larger than the radiation emitted by the process in addition to the InGaAs detector having a weaker response requires no additional discrimination. In FIG. 8, an off axis parabolic mirror 206 is illustrated to deflect the 1560 nm beam into detector 204. OAP 206 provides additional beam focusing that reduces the spot size to allow a smaller diameter iris for improved background rejection. Note that it s not required that reflectors 206 and 208 be OAPs, but they are preferred for their ability to both reflect and focus.

In the achromat lenses illustrated in FIGS. 7 and 8, lenses 201a and 201b are separated either by an air gap, or by a cement. An air gap is preferred for high temperature applications, but the tradeoff is that it is not the best choice for reducing optical reflections. The use of a "cemented" achromat lens is beneficial for optical reflections, but not as good for high temperature applications. Most cemented achromat lenses are limited to use in temperatures of up to 100° C.

Using either configuration illustrated in FIG. 7 or 8, and using optical components that are readily available, the receiver module footprint may be constructed to be on the order of 16 inches (40 cm) long and 12 to 16 inches (30 to 40 cm) wide. This size is well within the acceptable range for mounting a receiving unit on an industrial process. Higher dispersion between the two beams using different optic specifications, e.g., decreasing the convex mirror 202 focal length can result in an increase in the system footprint. Therefore dispersion and overall system size becomes a tradeoff. The three-component receiver modules illustrated in FIGS. 7 and 8 provide zero order dispersion, easy alignment, and insensitivity to beam steering and misalignment effects. The detail design specifications for the receiver optical components are preferably obtained from Optical Design Services, Tucson, Ariz. A company such as Optimax Systems Inc., Ontario, N.Y., then uses the specifications and fabricates the receiver optical components.

EXAMPLES

Example 1

Using the receiver module illustrated in FIG. 8, sample sets of data were collected from an industrial 30 MW furnace installation and on a 500 kW pilot furnace. For the industrial furnace, the beam launch system illustrated in FIG. 6 was employed with a 48 foot (14.6 meters) pathlength across the process to the receiver module. In this case, $O_2$ and $H_2O$ were detected in the process by scanning a diode laser at 200 Hz over a wavelength range to collect the full lineshape. A detailed description of the monitoring methodology is described in assignee's copending published patent application 20020031737, Ser. No. 09/964,017, published Mar. 14, 2002, incorporated herein by reference. The resulting absorbance spectrum for $O_2$ monitoring is illustrated in FIG. 9, with absorbance defined as $$A = \epsilon l c$$

Where A is the absorbance, $\epsilon$ is the absorptivity, l is the pathlength, and c is the concentration of the species being monitored. This relationship comes directly out of Beer's Law. The raw data for the spectrum of FIG. 9 is listed in Table 2. The concentration of $O_2$ is determined by integrating the area under the curve, knowing the linestrength for $O_2$ absorption transition and temperature. Therefore, before the $O_2$ concentration can be determined the gas temperature must be determined. For the multi-species monitoring system, gas temperature is obtained from the $H_2O$ absorbance spectrum, which is collected simultaneously or nearly simultaneously with the $O_2$ spectrum. In this example, the $H_2O$ spectrum collected is illustrated in FIG. 10 with the raw data listed in Table 3. As in the case of the $O_2$ spectrum the laser scan rate is 200 Hz, thus the spectrum shown in FIGS. 9 and 10 represent 200 averaged spectra. The gas temperature is obtained from the $H_2O$ spectrum by ratioing the area under peaks A and B and using an empirical formula that was obtained by conducting a calibration under controlled conditions, i.e., known temperature and $H_2O$ concentration. In this example, the temperature was determined to be 1547 K, resulting in an $O_2$ concentration of 5.95% and a $H_2O$ concentration of 7.58%.

Example 2

An example illustrating simultaneous $H_2O$ concentration, gas temperature and CO concentration from a 500 kW pilot furnace is illustrated in FIG. 11, with the raw data listed in Table 4. In this example, the furnace pathlength as only 1 foot (30.5 cm) and no $O_2$ was present. (Note, the spectral region and simultaneous detection of $H_2O$ and CO in this region is discussed in assignee's U.S. Provisional Application No. 60/349,638, filed Jan. 17, 2002, incorporated herein by reference. In this example, the gas temperature was 1387 K based on the $H_2O$ peaks A and B resulting in a CO concentration of 4.7%. In addition, the $H_2O$ concentration based on peak A, 36.6% for this example can also be obtained.

Examples 1 and 2 illustrate the multi-species detection capabilities of the apparatus of the invention under industrial operating conditions where high levels of background radiation are present, strong thermal gradients are present resulting in the beam spatial position changing in time, and attenuation effects are present due to particulate matter.

Distances between optical components for the receiver module of FIG. 8 are listed in Table 1. The dimensions are relative to the entrance window center (y=0, z=0). The y and z values listed are relative to the center of each optic component at the surface in the direction of the propagating beam, in other words, form left to right in FIG. 8.

Although the description herein is intended to be representative of the invention, it is not intended to limit the scope of the appended claims. While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

TABLE 1

Optical Component Configuration for Examples, FIG. 8

| Optical Element | Y (mm) | Z (mm) |
|---|---|---|
| Prism (200) | | |
| Surface 1 | 0.00 | 40.00 |
| Surface 2 | 2.90 | 60.78 |
| Achromat Lens (201) | | |
| Spherical lens | | |
| Element (201a) | | |
| Surface 1 | 16.40 | 107.21 |
| Surface 2 | 22.68 | 128.92 |
| Concave lens Element (201b) | | |
| Surface 1 | 22.97 | 129.91 |
| Surface 2 | 24.36 | 134.71 |
| Spherical mirror (202) | | |
| Surface 1 | 104.12 | 371.62 |

TABLE 2

Recorded absorbance values for oxygen monitoring referenced to spectrum in FIG. 9. Dispersion value for each channel is $1.39 \times 10^{-3}$ cm$^{-1}$.

| Channel # | Absorbance |
|---|---|
| 0 | −2.0635E−04 |
| 1 | −5.0784E−06 |
| 2 | 6.1479E−05 |

TABLE 2-continued

Recorded absorbance values for oxygen monitoring referenced to spectrum in FIG. 9. Dispersion value for each channel is $1.39 \times 10^{-3}$ cm$^{-1}$.

| Channel # | Absorbance |
|---|---|
| 3 | 4.8688E−06 |
| 4 | −1.6310E−04 |
| 5 | −2.4419E−04 |
| 6 | −1.5129E−04 |
| 7 | 5.1808E−06 |
| 8 | 2.1229E−05 |
| 9 | 2.5064E−05 |
| 10 | −6.4891E−05 |
| 11 | 3.6957E−05 |
| 12 | 1.7335E−04 |
| 13 | 2.6268E−04 |
| 14 | 1.9980E−04 |
| 15 | 1.0734E−04 |
| 16 | 6.7003E−05 |
| 17 | 7.2896E−05 |
| 18 | 1.3672E−04 |
| 19 | 1.2435E−04 |
| 20 | −2.8173E−05 |
| 21 | −1.7898E−05 |
| 22 | 5.6126E−05 |
| 23 | 2.1156E−04 |
| 24 | 2.7930E−04 |
| 25 | 1.6007E−04 |
| 26 | 1.3394E−04 |
| 27 | 1.2507E−04 |
| 28 | 1.3345E−04 |
| 29 | −1.5690E−05 |
| 30 | −1.4158E−04 |
| 32 | −2.7249E−05 |
| 33 | −4.8915E−05 |
| 34 | −6.6780E−06 |
| 35 | −2.8605E−05 |
| 36 | −6.2310E−05 |
| 37 | −7.2853E−05 |
| 38 | −4.8549E−05 |
| 39 | −1.1165E−04 |
| 40 | −1.4569E−04 |
| 41 | −1.6819E−04 |
| 42 | −2.0817E−04 |
| 43 | −2.5981E−04 |
| 44 | −1.7199E−04 |
| 45 | −2.0047E−04 |
| 46 | −1.5920E−04 |
| 47 | −1.4701E−04 |
| 48 | −2.1041E−04 |
| 49 | −1.1099E−04 |
| 50 | −9.8770E−05 |
| 51 | −1.1565E−04 |
| 52 | −8.0124E−05 |
| 53 | −9.1109E−05 |
| 54 | −8.4608E−05 |
| 55 | −7.2245E−05 |
| 56 | −7.1462E−05 |
| 57 | −7.6435E−06 |
| 58 | −1.7336E−05 |
| 59 | 9.4304E−05 |
| 60 | 1.3615E−04 |
| 61 | 1.3728E−04 |
| 62 | 1.2685E−04 |
| 63 | 1.2233E−04 |
| 64 | 1.2374E−04 |
| 65 | 1.1942E−04 |
| 66 | 1.4432E−04 |
| 67 | 2.2766E−04 |
| 68 | 1.3039E−04 |
| 69 | 5.0772E−05 |
| 70 | 8.7783E−05 |
| 71 | 4.3349E−05 |
| 72 | 3.4015E−05 |
| 73 | 3.0630E−05 |
| 74 | 2.1555E−06 |
| 75 | 9.9964E−05 |
| 76 | 7.3666E−05 |
| 77 | −2.8169E−05 |
| 78 | −3.0876E−05 |
| 79 | −4.3368E−06 |
| 80 | −6.7606E−06 |
| 82 | −9.8457E−06 |
| 83 | −1.0625E−04 |
| 84 | 2.4304E−06 |
| 85 | 6.5592E−06 |
| 86 | −4.7337E−05 |
| 87 | −8.3621E−05 |
| 88 | 4.8959E−05 |
| 89 | 8.2809E−05 |
| 90 | −6.3606E−05 |
| 91 | −1.1670E−04 |
| 92 | −1.2659E−05 |
| 93 | 7.9973E−05 |
| 94 | 5.6384E−05 |
| 95 | −7.7587E−05 |
| 96 | −7.8065E−06 |
| 97 | 1.7858E−04 |
| 98 | 1.5556E−04 |
| 99 | 4.6934E−06 |
| 100 | 1.1098E−05 |
| 101 | 2.0390E−04 |
| 102 | 1.8147E−04 |
| 103 | 2.1153E−06 |
| 104 | 4.4008E−05 |
| 105 | 2.1994E−04 |
| 106 | 3.4376E−04 |
| 107 | 1.8224E−04 |
| 108 | −9.5158E−05 |
| 109 | −6.0991E−06 |
| 110 | 1.4713E−04 |
| 111 | −1.9248E−06 |
| 112 | −1.4483E−04 |
| 113 | −7.8531E−05 |
| 114 | 1.5073E−04 |
| 115 | 9.5263E−05 |
| 116 | −1.6335E−04 |
| 117 | −2.3582E−04 |
| 118 | −5.2817E−05 |
| 119 | −3.1642E−06 |
| 120 | −2.4361E−04 |
| 121 | −2.9816E−04 |
| 122 | −8.0018E−05 |
| 123 | 8.6258E−05 |
| 124 | −1.5964E−04 |
| 125 | −2.4855E−04 |
| 126 | −8.2191E−05 |
| 127 | 4.3795E−05 |
| 128 | 7.3152E−06 |
| 129 | −1.2190E−04 |
| 130 | −6.5309E−05 |
| 132 | 2.4911E−05 |
| 133 | −9.8100E−05 |
| 134 | 4.5852E−05 |
| 135 | 1.6679E−04 |
| 136 | 3.2287E−05 |
| 137 | −1.2516E−04 |
| 138 | 5.9675E−05 |
| 139 | 1.8086E−04 |
| 140 | 2.3481E−05 |
| 141 | −1.4520E−04 |
| 142 | −2.9815E−05 |
| 143 | 3.3532E−05 |
| 144 | −4.2241E−05 |
| 145 | −2.5200E−05 |
| 146 | 1.7170E−04 |
| 147 | 2.0628E−04 |
| 148 | 5.5214E−05 |
| 149 | 9.5627E−05 |

TABLE 2-continued

Recorded absorbance values for oxygen monitoring referenced to spectrum in FIG. 9. Dispersion value for each channel is $1.39 \times 10^{-3}$ cm$^{-1}$.

| Channel # | Absorbance |
|---|---|
| 150 | 1.3611E−04 |
| 151 | 8.9629E−05 |
| 152 | 7.7970E−05 |
| 153 | 2.0555E−04 |
| 154 | 2.6938E−04 |
| 155 | 2.5780E−04 |
| 156 | 2.7525E−04 |
| 157 | 3.9726E−04 |
| 158 | 4.0894E−04 |
| 159 | 4.3226E−04 |
| 160 | 4.8465E−04 |
| 161 | 5.3125E−04 |
| 162 | 4.0933E−04 |
| 163 | 4.2689E−04 |
| 164 | 5.3738E−04 |
| 165 | 5.2006E−04 |
| 166 | 5.2018E−04 |
| 167 | 6.0165E−04 |
| 168 | 6.5988E−04 |
| 169 | 5.9601E−04 |
| 170 | 6.3094E−04 |
| 171 | 6.8331E−04 |
| 172 | 7.1243E−04 |
| 173 | 6.6012E−04 |
| 174 | 7.5314E−04 |
| 175 | 7.7638E−04 |
| 176 | 7.7049E−04 |
| 177 | 7.0644E−04 |
| 178 | 7.4703E−04 |
| 179 | 8.0502E−04 |
| 180 | 7.9902E−04 |
| 182 | 9.3231E−04 |
| 183 | 9.4364E−04 |
| 184 | 1.0015E−03 |
| 185 | 1.1001E−03 |
| 186 | 1.1929E−03 |
| 187 | 1.1807E−03 |
| 188 | 1.2676E−03 |
| 189 | 1.3836E−03 |
| 190 | 1.4238E−03 |
| 191 | 1.4172E−03 |
| 192 | 1.6618E−03 |
| 193 | 1.7603E−03 |
| 194 | 1.8413E−03 |
| 195 | 1.9692E−03 |
| 196 | 2.1733E−03 |
| 197 | 2.3248E−03 |
| 198 | 2.4234E−03 |
| 199 | 2.5162E−03 |
| 200 | 2.7974E−03 |
| 201 | 2.9787E−03 |
| 202 | 3.0066E−03 |
| 203 | 3.1880E−03 |
| 204 | 3.5057E−03 |
| 205 | 3.6342E−03 |
| 206 | 3.6857E−03 |
| 207 | 3.8735E−03 |
| 208 | 4.1210E−03 |
| 209 | 4.3212E−03 |
| 210 | 4.4083E−03 |
| 211 | 4.7459E−03 |
| 212 | 5.0483E−03 |
| 213 | 5.3093E−03 |
| 214 | 5.3787E−03 |
| 215 | 5.6521E−03 |
| 216 | 5.9681E−03 |
| 217 | 6.1278E−03 |
| 218 | 6.2816E−03 |
| 219 | 6.5684E−03 |
| 220 | 6.8012E−03 |
| 221 | 6.9796E−03 |
| 222 | 7.0672E−03 |
| 223 | 7.3491E−03 |
| 224 | 7.6983E−03 |
| 225 | 7.9080E−03 |
| 226 | 8.0690E−03 |
| 227 | 8.2912E−03 |
| 228 | 8.5687E−03 |
| 229 | 8.8038E−03 |
| 230 | 8.8610E−03 |
| 232 | 9.1904E−03 |
| 233 | 9.3337E−03 |
| 234 | 9.4216E−03 |
| 235 | 9.4602E−03 |
| 236 | 9.7083E−03 |
| 237 | 9.8332E−03 |
| 238 | 9.8470E−03 |
| 239 | 9.8237E−03 |
| 240 | 9.9176E−03 |
| 241 | 9.9559E−03 |
| 242 | 9.9262E−03 |
| 243 | 9.9274E−03 |
| 244 | 9.9902E−03 |
| 245 | 9.9727E−03 |
| 246 | 9.8748E−03 |
| 247 | 9.7709E−03 |
| 248 | 9.8272E−03 |
| 249 | 9.7232E−03 |
| 250 | 9.4837E−03 |
| 251 | 9.3490E−03 |
| 252 | 9.2452E−03 |
| 253 | 8.9757E−03 |
| 254 | 8.6639E−03 |
| 255 | 8.4809E−03 |
| 256 | 8.2982E−03 |
| 257 | 8.1340E−03 |
| 258 | 7.8481E−03 |
| 259 | 7.6479E−03 |
| 260 | 7.4297E−03 |
| 261 | 7.1209E−03 |
| 262 | 6.9337E−03 |
| 263 | 6.7226E−03 |
| 264 | 6.4575E−03 |
| 265 | 6.1328E−03 |
| 266 | 5.8508E−03 |
| 267 | 5.6473E−03 |
| 268 | 5.2587E−03 |
| 269 | 4.9248E−03 |
| 270 | 4.7107E−03 |
| 271 | 4.5504E−03 |
| 272 | 4.3072E−03 |
| 273 | 4.0823E−03 |
| 274 | 3.8991E−03 |
| 275 | 3.6276E−03 |
| 276 | 3.3448E−03 |
| 277 | 3.2568E−03 |
| 278 | 3.0925E−03 |
| 279 | 2.8402E−03 |
| 280 | 2.7585E−03 |
| 282 | 2.3670E−03 |
| 283 | 2.2622E−03 |
| 284 | 2.1517E−03 |
| 285 | 1.9364E−03 |
| 286 | 1.7855E−03 |
| 287 | 1.7337E−03 |
| 288 | 1.6703E−03 |
| 289 | 1.4792E−03 |
| 290 | 1.4102E−03 |
| 291 | 1.3992E−03 |
| 292 | 1.2666E−03 |
| 293 | 1.1168E−03 |
| 294 | 1.1813E−03 |
| 295 | 1.1069E−03 |
| 296 | 9.1114E−04 |

TABLE 2-continued

Recorded absorbance values for oxygen monitoring referenced to spectrum in FIG. 9. Dispersion value for each channel is $1.39 \times 10^{-3}$ cm$^{-1}$.

| Channel # | Absorbance |
| --- | --- |
| 297 | 8.7166E−04 |
| 298 | 8.4378E−04 |
| 299 | 7.8710E−04 |
| 300 | 6.0367E−04 |
| 301 | 6.3365E−04 |
| 302 | 5.5998E−04 |
| 303 | 4.0009E−04 |
| 304 | 3.7269E−04 |
| 305 | 4.0290E−04 |
| 306 | 3.6990E−04 |
| 307 | 2.4502E−04 |
| 308 | 2.3517E−04 |
| 309 | 2.8286E−04 |
| 310 | 1.8126E−04 |
| 311 | 1.0853E−04 |
| 312 | 1.9084E−04 |
| 313 | 1.6994E−04 |
| 314 | 9.7464E−05 |
| 315 | 7.6721E−05 |
| 316 | 1.9950E−04 |
| 317 | 1.7891E−04 |
| 318 | 1.0679E−04 |
| 319 | 1.3803E−04 |
| 320 | 1.7508E−04 |
| 321 | 1.6634E−04 |
| 322 | −1.4274E−05 |
| 323 | 1.7305E−05 |
| 324 | 1.6362E−04 |
| 325 | 1.7820E−04 |
| 326 | 4.3836E−05 |
| 327 | 9.2983E−05 |
| 328 | 1.5943E−04 |
| 329 | 1.1135E−04 |
| 330 | −3.3972E−05 |
| 332 | 3.6504E−05 |
| 333 | 3.4685E−05 |
| 334 | −5.2883E−05 |
| 335 | −1.4464E−05 |
| 336 | 9.2799E−05 |
| 337 | −5.9549E−06 |
| 338 | −5.8773E−05 |
| 339 | 1.4387E−05 |
| 340 | 1.1057E−04 |
| 341 | 9.2345E−05 |
| 342 | 3.4192E−05 |
| 343 | −1.2421E−05 |
| 344 | 6.6935E−05 |
| 345 | 1.0063E−04 |
| 346 | −1.4359E−05 |
| 347 | −2.0527E−05 |
| 348 | 2.4845E−05 |
| 349 | −9.7419E−06 |
| 350 | −7.8513E−05 |
| 351 | −1.6429E−04 |
| 352 | −9.0074E−05 |
| 353 | −5.5741E−05 |
| 354 | −1.3557E−04 |
| 355 | −1.4676E−04 |
| 356 | −9.5113E−05 |
| 357 | −7.7646E−05 |
| 358 | −1.6285E−04 |
| 359 | −1.2243E−04 |
| 360 | −7.6245E−05 |
| 361 | −4.7135E−05 |
| 362 | −1.0356E−04 |
| 363 | −9.7166E−05 |
| 364 | 1.1981E−05 |
| 365 | 4.1269E−05 |
| 366 | −6.0663E−05 |
| 367 | −4.2733E−05 |
| 368 | 6.6535E−05 |
| 369 | 6.1684E−05 |
| 370 | 1.1169E−06 |
| 371 | 5.1993E−05 |
| 372 | 8.1390E−05 |
| 373 | 2.5204E−05 |
| 374 | −6.5193E−05 |
| 375 | −3.5855E−05 |
| 376 | −1.7916E−05 |
| 377 | −8.5527E−05 |
| 378 | −3.9211E−05 |
| 379 | 4.7003E−05 |
| 380 | 1.3432E−05 |
| 382 | 7.7223E−05 |
| 383 | 6.6251E−05 |
| 384 | 1.5273E−05 |
| 385 | −7.2831E−06 |
| 386 | 2.7044E−05 |
| 387 | −6.4083E−05 |
| 388 | −9.8339E−05 |
| 389 | 4.3769E−05 |
| 390 | 2.6296E−05 |
| 391 | −2.7346E−06 |
| 392 | 1.9313E−05 |
| 393 | 4.6873E−05 |
| 394 | 3.4397E−05 |
| 395 | −1.8152E−05 |
| 396 | −8.2836E−06 |
| 397 | 6.3990E−05 |
| 398 | 3.9219E−05 |
| 399 | 8.8217E−05 |
| 400 | 1.3696E−04 |
| 401 | 1.2847E−04 |
| 402 | 4.5638E−05 |
| 403 | 6.5016E−05 |
| 404 | 1.4667E−04 |
| 405 | 6.8574E−05 |
| 406 | 7.5525E−05 |
| 407 | 4.7953E−05 |
| 408 | −1.9790E−05 |
| 409 | −5.3812E−05 |
| 410 | −2.5726E−05 |
| 411 | −9.4710E−05 |
| 412 | −9.5932E−05 |
| 413 | −3.5101E−05 |
| 414 | 2.4786E−06 |
| 415 | −4.5713E−05 |
| 416 | −8.8738E−05 |
| 417 | −7.2787E−06 |
| 418 | 3.9523E−05 |
| 419 | −4.5047E−05 |
| 420 | −6.1986E−05 |
| 421 | 4.5490E−05 |
| 422 | −7.5096E−05 |
| 423 | 1.8670E−06 |
| 424 | 5.2758E−08 |
| 425 | 5.3899E−07 |
| 426 | 9.6381E−07 |
| 427 | −4.0139E−08 |
| 428 | −7.9427E−07 |
| 429 | −4.3056E−07 |
| 430 | −4.2744E−09 |
| 432 | −7.0102E−07 |
| 433 | 2.8529E−07 |
| 434 | −2.7842E−07 |
| 435 | −1.3991E−06 |
| 436 | −5.3527E−07 |
| 437 | −4.2601E−08 |

TABLE 3

Recorded absorbance values for H$_2$O monitoring referenced to spectrum in FIG. 10. Dispersion value for each channel is $2.58 \times 10^{-3}$ cm$^{-1}$.

| Channel # | Absorbance |
|---|---|
| 0 | 9.6969E−04 |
| 1 | 6.7374E−04 |
| 2 | 3.2638E−04 |
| 3 | 1.8694E−04 |
| 4 | −1.0781E−04 |
| 5 | −2.4667E−04 |
| 6 | −2.8203E−04 |
| 7 | −6.7917E−04 |
| 8 | −8.6887E−04 |
| 9 | −9.5499E−04 |
| 10 | −1.0927E−03 |
| 11 | −1.1268E−03 |
| 12 | −1.1092E−03 |
| 13 | −1.4010E−03 |
| 14 | −1.5891E−03 |
| 15 | −1.6224E−03 |
| 16 | −1.6558E−03 |
| 17 | −1.8946E−03 |
| 18 | −1.6701E−03 |
| 19 | −1.6514E−03 |
| 20 | −1.7354E−03 |
| 21 | −1.4592E−03 |
| 22 | −1.6458E−03 |
| 23 | −1.1641E−03 |
| 24 | −1.0933E−03 |
| 25 | −8.6860E−04 |
| 26 | −7.4635E−04 |
| 27 | −3.1600E−04 |
| 28 | −9.1233E−05 |
| 29 | 3.9066E−04 |
| 30 | 7.6966E−04 |
| 31 | 1.1487E−03 |
| 32 | 1.7331E−03 |
| 33 | 2.1634E−03 |
| 34 | 2.9535E−03 |
| 35 | 3.8469E−03 |
| 36 | 4.3801E−03 |
| 37 | 5.5309E−03 |
| 38 | 6.3217E−03 |
| 39 | 7.4219E−03 |
| 40 | 8.5741E−03 |
| 41 | 9.5206E−03 |
| 42 | 1.0984E−02 |
| 43 | 1.2396E−02 |
| 44 | 1.3913E−02 |
| 45 | 1.5483E−02 |
| 46 | 1.7158E−02 |
| 47 | 1.9198E−02 |
| 48 | 2.1137E−02 |
| 49 | 2.3599E−02 |
| 50 | 2.5909E−02 |
| 51 | 2.8640E−02 |
| 52 | 3.1114E−02 |
| 53 | 3.4381E−02 |
| 54 | 3.7497E−02 |
| 55 | 4.0620E−02 |
| 56 | 4.4226E−02 |
| 57 | 4.8373E−02 |
| 58 | 5.2426E−02 |
| 59 | 5.6972E−02 |
| 60 | 6.1587E−02 |
| 61 | 6.6326E−02 |
| 62 | 7.1405E−02 |
| 63 | 7.6885E−02 |
| 64 | 8.1567E−02 |
| 65 | 8.7031E−02 |
| 66 | 9.2022E−02 |
| 67 | 9.6975E−02 |
| 68 | 1.0106E−01 |
| 69 | 1.0482E−01 |
| 70 | 1.0781E−01 |
| 71 | 1.0986E−01 |
| 72 | 1.1074E−01 |
| 73 | 1.1107E−01 |
| 74 | 1.1000E−01 |
| 75 | 1.0821E−01 |
| 76 | 1.0520E−01 |
| 77 | 1.0165E−01 |
| 78 | 9.7066E−02 |
| 79 | 9.2885E−02 |
| 80 | 8.8013E−02 |
| 81 | 8.3380E−02 |
| 82 | 7.9040E−02 |
| 83 | 7.4502E−02 |
| 84 | 7.0844E−02 |
| 85 | 6.7147E−02 |
| 86 | 6.4265E−02 |
| 87 | 6.1339E−02 |
| 88 | 5.9219E−02 |
| 89 | 5.6733E−02 |
| 90 | 5.5259E−02 |
| 91 | 5.3683E−02 |
| 92 | 5.2268E−02 |
| 93 | 5.1014E−02 |
| 94 | 4.9605E−02 |
| 95 | 4.8513E−02 |
| 96 | 4.7423E−02 |
| 97 | 4.6126E−02 |
| 98 | 4.4571E−02 |
| 99 | 4.3227E−02 |
| 100 | 4.1626E−02 |
| 101 | 4.0184E−02 |
| 102 | 3.8019E−02 |
| 103 | 3.6326E−02 |
| 104 | 3.4430E−02 |
| 105 | 3.2385E−02 |
| 106 | 3.0602E−02 |
| 107 | 2.8515E−02 |
| 108 | 2.6998E−02 |
| 109 | 2.5075E−02 |
| 110 | 2.3667E−02 |
| 111 | 2.2059E−02 |
| 112 | 2.0911E−02 |
| 113 | 1.9563E−02 |
| 114 | 1.8319E−02 |
| 115 | 1.7382E−02 |
| 116 | 1.6547E−02 |
| 117 | 1.5764E−02 |
| 118 | 1.5336E−02 |
| 119 | 1.4908E−02 |
| 120 | 1.4329E−02 |
| 121 | 1.4004E−02 |
| 122 | 1.3729E−02 |
| 123 | 1.3303E−02 |
| 124 | 1.2979E−02 |
| 125 | 1.2605E−02 |
| 126 | 1.2231E−02 |
| 127 | 1.1708E−02 |
| 128 | 1.1136E−02 |
| 129 | 1.0764E−02 |
| 130 | 1.0044E−02 |
| 131 | 9.4239E−03 |
| 132 | 8.7055E−03 |
| 133 | 8.1377E−03 |
| 134 | 7.5710E−03 |
| 135 | 6.7564E−03 |
| 136 | 6.2413E−03 |
| 137 | 5.8758E−03 |
| 138 | 5.5604E−03 |
| 139 | 4.8988E−03 |
| 140 | 4.7825E−03 |
| 141 | 4.6172E−03 |
| 142 | 4.4520E−03 |
| 143 | 4.1886E−03 |
| 144 | 4.3205E−03 |
| 145 | 4.4031E−03 |

TABLE 3-continued

Recorded absorbance values for H$_2$O monitoring referenced to spectrum in FIG. 10. Dispersion value for each channel is 2.58 × 10$^{-3}$ cm$^{-1}$.

| Channel # | Absorbance |
|---|---|
| 146 | 4.5845E−03 |
| 147 | 5.0130E−03 |
| 148 | 5.1451E−03 |
| 149 | 5.3759E−03 |
| 150 | 5.8538E−03 |
| 151 | 6.0846E−03 |
| 152 | 6.3156E−03 |
| 153 | 6.8919E−03 |
| 154 | 7.2709E−03 |
| 155 | 7.4526E−03 |
| 156 | 7.7330E−03 |
| 157 | 8.1613E−03 |
| 158 | 8.4910E−03 |
| 159 | 8.4751E−03 |
| 160 | 8.6076E−03 |
| 161 | 8.5430E−03 |
| 162 | 8.5770E−03 |
| 163 | 8.2170E−03 |
| 164 | 7.9070E−03 |
| 165 | 7.3517E−03 |
| 166 | 7.3376E−03 |
| 167 | 6.5871E−03 |
| 168 | 6.0832E−03 |
| 169 | 5.6781E−03 |
| 170 | 5.0289E−03 |
| 171 | 4.8207E−03 |
| 172 | 4.5641E−03 |
| 173 | 4.0149E−03 |
| 174 | 3.8570E−03 |
| 175 | 3.6018E−03 |
| 176 | 3.4933E−03 |
| 177 | 3.5312E−03 |
| 178 | 3.7639E−03 |
| 179 | 3.9482E−03 |
| 180 | 4.2296E−03 |
| 181 | 4.5113E−03 |
| 182 | 5.1339E−03 |
| 183 | 5.6103E−03 |
| 184 | 6.2816E−03 |
| 185 | 7.1969E−03 |
| 186 | 8.2588E−03 |
| 187 | 9.2721E−03 |
| 188 | 1.0286E−02 |
| 189 | 1.1594E−02 |
| 190 | 1.2658E−02 |
| 191 | 1.3967E−02 |
| 192 | 1.4542E−02 |
| 193 | 1.6785E−02 |
| 194 | 1.8048E−02 |
| 195 | 1.9410E−02 |
| 196 | 2.0675E−02 |
| 197 | 2.1941E−02 |
| 198 | 2.3108E−02 |
| 199 | 2.4277E−02 |
| 200 | 2.5298E−02 |
| 201 | 2.6319E−02 |
| 202 | 2.7192E−02 |
| 203 | 2.8264E−02 |
| 204 | 2.8692E−02 |
| 205 | 2.9665E−02 |
| 206 | 3.0341E−02 |
| 207 | 3.0621E−02 |
| 208 | 3.1248E−02 |
| 209 | 3.1776E−02 |
| 210 | 3.2105E−02 |
| 211 | 3.2236E−02 |
| 212 | 3.2170E−02 |
| 213 | 3.2054E−02 |
| 214 | 3.1790E−02 |
| 215 | 3.1773E−02 |
| 216 | 3.1214E−02 |
| 217 | 3.0408E−02 |
| 218 | 3.0146E−02 |
| 219 | 2.9146E−02 |
| 220 | 2.8148E−02 |
| 221 | 2.7397E−02 |
| 222 | 2.6451E−02 |
| 223 | 2.5214E−02 |
| 224 | 2.4028E−02 |
| 225 | 2.3137E−02 |
| 226 | 2.1469E−02 |
| 227 | 2.0340E−02 |
| 228 | 1.8922E−02 |
| 229 | 1.7652E−02 |
| 230 | 1.6434E−02 |
| 231 | 1.5219E−02 |
| 232 | 1.4006E−02 |
| 233 | 1.2700E−02 |
| 234 | 1.1781E−02 |
| 235 | 1.0529E−02 |
| 236 | 9.3746E−03 |
| 237 | 8.5097E−03 |
| 238 | 7.7899E−03 |
| 239 | 7.0236E−03 |
| 240 | 6.4017E−03 |
| 241 | 5.6858E−03 |
| 242 | 4.9712E−03 |
| 243 | 4.4477E−03 |
| 244 | 3.9727E−03 |
| 245 | 3.7353E−03 |
| 246 | 3.3090E−03 |
| 247 | 2.9778E−03 |
| 248 | 2.4584E−03 |
| 249 | 2.5538E−03 |
| 250 | 2.4131E−03 |
| 251 | 2.2257E−03 |
| 252 | 2.2272E−03 |
| 253 | 2.4174E−03 |
| 254 | 2.5606E−03 |
| 255 | 2.7040E−03 |
| 256 | 2.6116E−03 |
| 257 | 3.1321E−03 |
| 258 | 3.3696E−03 |
| 259 | 3.6544E−03 |
| 260 | 3.9863E−03 |
| 261 | 4.6481E−03 |
| 262 | 5.1213E−03 |
| 263 | 5.4061E−03 |
| 264 | 6.0677E−03 |
| 265 | 6.5882E−03 |
| 266 | 7.1086E−03 |
| 267 | 7.7235E−03 |
| 268 | 8.2912E−03 |
| 269 | 8.6702E−03 |
| 270 | 9.2850E−03 |
| 271 | 1.0089E−02 |
| 272 | 1.0704E−02 |
| 273 | 1.1508E−02 |
| 274 | 1.2312E−02 |
| 275 | 1.3259E−02 |
| 276 | 1.4300E−02 |
| 277 | 1.5200E−02 |
| 278 | 1.6100E−02 |
| 279 | 1.7665E−02 |
| 280 | 1.8661E−02 |
| 281 | 1.9752E−02 |
| 282 | 2.0939E−02 |
| 283 | 2.2080E−02 |
| 284 | 2.3173E−02 |
| 285 | 2.3933E−02 |
| 286 | 2.4741E−02 |
| 287 | 2.5597E−02 |
| 288 | 2.6119E−02 |
| 289 | 2.6737E−02 |
| 290 | 2.7164E−02 |
| 291 | 2.7591E−02 |

TABLE 3-continued

Recorded absorbance values for H$_2$O monitoring referenced to spectrum in FIG. 10. Dispersion value for each channel is 2.58 × 10$^{-3}$ cm$^{-1}$.

| Channel # | Absorbance |
|---|---|
| 292 | 2.7683E-02 |
| 293 | 2.8014E-02 |
| 294 | 2.7964E-02 |
| 295 | 2.7819E-02 |
| 296 | 2.8245E-02 |
| 297 | 2.8529E-02 |
| 298 | 2.8241E-02 |
| 299 | 2.8429E-02 |
| 300 | 2.8428E-02 |
| 301 | 2.8426E-02 |
| 302 | 2.8282E-02 |
| 303 | 2.8233E-02 |
| 304 | 2.8089E-02 |
| 305 | 2.7566E-02 |
| 306 | 2.7423E-02 |
| 307 | 2.6760E-02 |
| 308 | 2.6192E-02 |
| 309 | 2.5625E-02 |
| 310 | 2.4209E-02 |
| 311 | 2.3221E-02 |
| 312 | 2.2047E-02 |
| 313 | 2.0829E-02 |
| 314 | 1.9660E-02 |
| 315 | 1.8214E-02 |
| 316 | 1.6958E-02 |
| 317 | 1.5565E-02 |
| 318 | 1.4595E-02 |
| 319 | 1.3208E-02 |
| 320 | 1.2104E-02 |
| 321 | 1.1186E-02 |
| 322 | 1.0225E-02 |
| 323 | 9.2654E-03 |
| 324 | 8.5843E-03 |
| 325 | 7.9507E-03 |
| 326 | 7.4101E-03 |
| 327 | 6.8707E-03 |
| 328 | 6.5614E-03 |
| 329 | 5.9778E-03 |
| 330 | 5.5782E-03 |
| 331 | 5.4539E-03 |
| 332 | 4.9642E-03 |
| 333 | 4.7037E-03 |
| 334 | 4.2155E-03 |
| 335 | 3.7284E-03 |
| 336 | 3.5152E-03 |
| 337 | 3.2569E-03 |
| 338 | 2.9082E-03 |
| 339 | 2.6056E-03 |
| 340 | 2.2580E-03 |
| 341 | 2.0472E-03 |
| 342 | 1.6557E-03 |
| 343 | 1.4458E-03 |
| 344 | 1.0555E-03 |
| 345 | 7.1111E-04 |
| 346 | 2.3178E-04 |
| 347 | -2.4666E-04 |
| 348 | -4.5380E-04 |
| 349 | -7.5054E-04 |
| 350 | -1.1816E-03 |
| 351 | -1.4771E-03 |
| 352 | -1.7272E-03 |
| 353 | -1.9319E-03 |
| 354 | -2.2259E-03 |
| 355 | -2.7434E-03 |
| 356 | -2.9465E-03 |
| 357 | -2.9703E-03 |
| 358 | -3.3068E-03 |
| 359 | -3.4194E-03 |
| 360 | -3.7995E-03 |
| 361 | -3.9114E-03 |
| 362 | -4.0676E-03 |
| 363 | -4.1786E-03 |
| 364 | -4.3786E-03 |
| 365 | -4.5337E-03 |
| 366 | -4.7327E-03 |
| 367 | -4.8870E-03 |
| 368 | -4.8633E-03 |
| 369 | -4.7064E-03 |
| 370 | -4.9487E-03 |
| 371 | -4.8358E-03 |
| 372 | -4.7228E-03 |
| 373 | -4.8755E-03 |
| 374 | -4.6737E-03 |
| 375 | -4.4275E-03 |
| 376 | -4.3142E-03 |
| 377 | -4.2008E-03 |
| 378 | -3.8218E-03 |
| 379 | -3.9295E-03 |
| 380 | -3.8157E-03 |
| 381 | -3.2599E-03 |
| 382 | -3.2787E-03 |
| 383 | -3.0766E-03 |
| 384 | -3.0951E-03 |
| 385 | -2.8927E-03 |
| 386 | -2.9111E-03 |
| 387 | -2.7969E-03 |
| 388 | -2.6824E-03 |
| 389 | -2.7445E-03 |
| 390 | -2.8061E-03 |
| 391 | -3.0436E-03 |
| 392 | -3.1927E-03 |
| 393 | -3.4294E-03 |
| 394 | -3.7094E-03 |
| 395 | -3.8133E-03 |
| 396 | -3.9609E-03 |
| 397 | -4.2833E-03 |
| 398 | -4.6491E-03 |
| 399 | -4.3576E-03 |
| 400 | -4.9411E-03 |
| 401 | -5.0430E-03 |
| 402 | -5.1444E-03 |
| 403 | -5.2020E-03 |
| 404 | -5.3029E-03 |
| 405 | -5.2291E-03 |
| 406 | -5.3297E-03 |
| 407 | -5.2991E-03 |
| 408 | -5.1814E-03 |
| 409 | -5.0200E-03 |
| 410 | -4.8151E-03 |
| 411 | -4.6102E-03 |
| 412 | -4.2747E-03 |
| 413 | -3.9392E-03 |
| 414 | -3.6471E-03 |
| 415 | -3.3116E-03 |
| 416 | -2.9761E-03 |
| 417 | -2.6842E-03 |
| 418 | -2.3052E-03 |
| 419 | -2.0131E-03 |
| 420 | -1.7644E-03 |
| 421 | -1.3420E-03 |
| 422 | -1.2673E-03 |
| 423 | -1.1490E-03 |
| 424 | -7.2659E-04 |
| 425 | -5.6484E-04 |
| 426 | -5.3322E-04 |
| 427 | -1.9761E-04 |
| 428 | -4.6950E-04 |
| 429 | -9.0495E-05 |
| 430 | -2.3188E-04 |
| 431 | 6.0483E-05 |
| 432 | 6.2668E-06 |
| 433 | 8.2109E-05 |
| 434 | 2.0133E-04 |

TABLE 4

Recorded absorbance values for CO and H$_2$O monitoring referenced to spectrum in FIG. 11. Dispersion value for each channel is 2.58 ×10$^{-3}$ cm$^{-1}$.

| Channel # | Absorbance |
| --- | --- |
| 0 | 9.6969E−05 |
| 1 | 6.7374E−05 |
| 2 | 3.2638E−05 |
| 3 | 1.8694E−05 |
| 4 | −1.0781E−05 |
| 5 | −2.4667E−05 |
| 6 | −2.8203E−05 |
| 7 | −6.7917E−05 |
| 8 | −8.6887E−05 |
| 9 | −9.5499E−05 |
| 10 | −1.6094E−05 |
| 11 | −6.7056E−05 |
| 12 | 4.7727E−05 |
| 13 | −2.0327E−04 |
| 14 | −5.1860E−06 |
| 15 | −5.7742E−05 |
| 16 | 1.2466E−04 |
| 17 | −2.1998E−05 |
| 18 | 8.7111E−05 |
| 19 | 3.4418E−05 |
| 20 | 2.3741E−04 |
| 21 | 1.5846E−04 |
| 22 | 1.9432E−04 |
| 23 | 2.1447E−04 |
| 24 | 4.1209E−04 |
| 25 | 2.3902E−04 |
| 26 | 3.6856E−04 |
| 27 | 4.8247E−04 |
| 28 | 5.1803E−04 |
| 29 | 5.1700E−04 |
| 30 | 6.0466E−04 |
| 31 | 7.3411E−04 |
| 32 | 6.8064E−04 |
| 33 | 7.2639E−04 |
| 34 | 9.6024E−04 |
| 35 | 8.7520E−04 |
| 36 | 9.4171E−04 |
| 37 | 1.1442E−03 |
| 38 | 1.1530E−03 |
| 39 | 1.1671E−03 |
| 40 | 1.4010E−03 |
| 41 | 1.4254E−03 |
| 42 | 1.4603E−03 |
| 43 | 1.7048E−03 |
| 44 | 1.7501E−03 |
| 45 | 1.7847E−03 |
| 46 | 2.0716E−03 |
| 47 | 2.0957E−03 |
| 48 | 2.2091E−03 |
| 49 | 2.4227E−03 |
| 50 | 2.4782E−03 |
| 51 | 2.6550E−03 |
| 52 | 2.8372E−03 |
| 53 | 2.8820E−03 |
| 54 | 3.1120E−03 |
| 55 | 3.2573E−03 |
| 56 | 3.2914E−03 |
| 57 | 3.5323E−03 |
| 58 | 3.6619E−03 |
| 59 | 3.7170E−03 |
| 60 | 3.9743E−03 |
| 61 | 3.9389E−03 |
| 62 | 4.1165E−03 |
| 63 | 4.2994E−03 |
| 64 | 4.2744E−03 |
| 65 | 4.4307E−03 |
| 66 | 4.4429E−03 |
| 67 | 4.4710E−03 |
| 68 | 4.6593E−03 |
| 69 | 4.5165E−03 |
| 70 | 4.5979E−03 |
| 71 | 4.5885E−03 |
| 72 | 4.4778E−03 |
| 73 | 4.5909E−03 |
| 74 | 4.4004E−03 |
| 75 | 4.3432E−03 |
| 76 | 4.3284E−03 |
| 77 | 4.1650E−03 |
| 78 | 4.1927E−03 |
| 79 | 4.0402E−03 |
| 80 | 3.9302E−03 |
| 81 | 3.8997E−03 |
| 82 | 3.7372E−03 |
| 83 | 3.7488E−03 |
| 84 | 3.5656E−03 |
| 85 | 3.4773E−03 |
| 86 | 3.4363E−03 |
| 87 | 3.2119E−03 |
| 88 | 3.2549E−03 |
| 89 | 3.0518E−03 |
| 90 | 3.0006E−03 |
| 91 | 2.8973E−03 |
| 92 | 2.7108E−03 |
| 93 | 2.7483E−03 |
| 94 | 2.5569E−03 |
| 95 | 2.5787E−03 |
| 96 | 2.4604E−03 |
| 97 | 2.3266E−03 |
| 98 | 2.3277E−03 |
| 99 | 2.1270E−03 |
| 100 | 2.2003E−03 |
| 101 | 2.0877E−03 |
| 102 | 2.0371E−03 |
| 103 | 2.0225E−03 |
| 104 | 1.8587E−03 |
| 105 | 1.8699E−03 |
| 106 | 1.7218E−03 |
| 107 | 1.7022E−03 |
| 108 | 1.6517E−03 |
| 109 | 1.5604E−03 |
| 110 | 1.5919E−03 |
| 111 | 1.4444E−03 |
| 112 | 1.4503E−03 |
| 113 | 1.3081E−03 |
| 114 | 1.3038E−03 |
| 115 | 1.2383E−03 |
| 116 | 1.1932E−03 |
| 117 | 1.2651E−03 |
| 118 | 1.1335E−03 |
| 119 | 1.1697E−03 |
| 120 | 1.0586E−03 |
| 121 | 1.0338E−03 |
| 122 | 1.0090E−03 |
| 123 | 9.2849E−04 |
| 124 | 1.0100E−03 |
| 125 | 8.7384E−04 |
| 126 | 9.3501E−04 |
| 127 | 8.3431E−04 |
| 128 | 8.0946E−04 |
| 129 | 7.6442E−04 |
| 130 | 6.8914E−04 |
| 131 | 7.3987E−04 |
| 132 | 6.2936E−04 |
| 133 | 7.1021E−04 |
| 134 | 6.0477E−04 |
| 135 | 6.2007E−04 |
| 136 | 5.9009E−04 |
| 137 | 5.0991E−04 |
| 138 | 5.4518E−04 |
| 139 | 4.0489E−04 |
| 140 | 5.0020E−04 |
| 141 | 3.8504E−04 |
| 142 | 4.6517E−04 |
| 143 | 4.4510E−04 |
| 144 | 3.9003E−04 |
| 145 | 4.1493E−04 |

TABLE 4-continued

Recorded absorbance values for CO and H$_2$O monitoring referenced to spectrum in FIG. 11. Dispersion value for each channel is 2.58 ×10$^{-3}$ cm$^{-1}$.

| Channel # | Absorbance |
|---|---|
| 146 | 2.9991E−04 |
| 147 | 3.6469E−04 |
| 148 | 2.5474E−04 |
| 149 | 3.4434E−04 |
| 150 | 3.2911E−04 |
| 151 | 3.7369E−04 |
| 152 | 3.9331E−04 |
| 153 | 3.2813E−04 |
| 154 | 4.0744E−04 |
| 155 | 2.8251E−04 |
| 156 | 4.0150E−04 |
| 157 | 3.1139E−04 |
| 158 | 3.6555E−04 |
| 159 | 3.5500E−04 |
| 160 | 3.4443E−04 |
| 161 | 4.0838E−04 |
| 162 | 3.1821E−04 |
| 163 | 4.3170E−04 |
| 164 | 3.1669E−04 |
| 165 | 3.7543E−04 |
| 166 | 3.2992E−04 |
| 167 | 3.2902E−04 |
| 168 | 3.8756E−04 |
| 169 | 3.5685E−04 |
| 170 | 4.1528E−04 |
| 171 | 3.5972E−04 |
| 172 | 4.4777E−04 |
| 173 | 3.8719E−04 |
| 174 | 4.7017E−04 |
| 175 | 4.4416E−04 |
| 176 | 4.5279E−04 |
| 177 | 5.2075E−04 |
| 178 | 4.8474E−04 |
| 179 | 6.1198E−04 |
| 180 | 5.5112E−04 |
| 181 | 6.8817E−04 |
| 182 | 6.6182E−04 |
| 183 | 7.0473E−04 |
| 184 | 7.5256E−04 |
| 185 | 7.4091E−04 |
| 186 | 8.4308E−04 |
| 187 | 8.1650E−04 |
| 188 | 9.7306E−04 |
| 189 | 9.1663E−04 |
| 190 | 1.0434E−03 |
| 191 | 1.0562E−03 |
| 192 | 1.0194E−03 |
| 193 | 1.1807E−03 |
| 194 | 1.1389E−03 |
| 195 | 1.2456E−03 |
| 196 | 1.1789E−03 |
| 197 | 1.3004E−03 |
| 198 | 1.2385E−03 |
| 199 | 1.3252E−03 |
| 200 | 1.3326E−03 |
| 201 | 1.3548E−03 |
| 202 | 1.4414E−03 |
| 203 | 1.3347E−03 |
| 204 | 1.4558E−03 |
| 205 | 1.3837E−03 |
| 206 | 1.4354E−03 |
| 207 | 1.3980E−03 |
| 208 | 1.4643E−03 |
| 209 | 1.4416E−03 |
| 210 | 1.4239E−03 |
| 211 | 1.4654E−03 |
| 212 | 1.4130E−03 |
| 213 | 1.4889E−03 |
| 214 | 1.3673E−03 |
| 215 | 1.4283E−03 |
| 216 | 1.3414E−03 |
| 217 | 1.3431E−03 |
| 218 | 1.3251E−03 |
| 219 | 1.2431E−03 |
| 220 | 1.2989E−03 |
| 221 | 1.1629E−03 |
| 222 | 1.2382E−03 |
| 223 | 1.1169E−03 |
| 224 | 1.1577E−03 |
| 225 | 1.0906E−03 |
| 226 | 1.0675E−03 |
| 227 | 1.0788E−03 |
| 228 | 9.6759E−04 |
| 229 | 9.8362E−04 |
| 230 | 8.5308E−04 |
| 231 | 9.1786E−04 |
| 232 | 8.2154E−04 |
| 233 | 8.2767E−04 |
| 234 | 7.9477E−04 |
| 235 | 7.5699E−04 |
| 236 | 7.8249E−04 |
| 237 | 6.7173E−04 |
| 238 | 7.4576E−04 |
| 239 | 6.1076E−04 |
| 240 | 6.7976E−04 |
| 241 | 6.1278E−04 |
| 242 | 6.1858E−04 |
| 243 | 6.2920E−04 |
| 244 | 6.0582E−04 |
| 245 | 6.5998E−04 |
| 246 | 5.6870E−04 |
| 247 | 6.5180E−04 |
| 248 | 5.8955E−04 |
| 249 | 6.3863E−04 |
| 250 | 6.0054E−04 |
| 251 | 6.2048E−04 |
| 252 | 6.6938E−04 |
| 253 | 6.2635E−04 |
| 254 | 7.2835E−04 |
| 255 | 6.6105E−04 |
| 256 | 7.3876E−04 |
| 257 | 7.2456E−04 |
| 258 | 7.6348E−04 |
| 259 | 7.6852E−04 |
| 260 | 7.9285E−04 |
| 261 | 8.5579E−04 |
| 262 | 8.0272E−04 |
| 263 | 9.4770E−04 |
| 264 | 8.9449E−04 |
| 265 | 1.0152E−03 |
| 266 | 9.7158E−04 |
| 267 | 1.0052E−03 |
| 268 | 1.0388E−03 |
| 269 | 9.7574E−04 |
| 270 | 1.0575E−03 |
| 271 | 1.0137E−03 |
| 272 | 1.1050E−03 |
| 273 | 1.0563E−03 |
| 274 | 1.1523E−03 |
| 275 | 1.1469E−03 |
| 276 | 1.1608E−03 |
| 277 | 1.2181E−03 |
| 278 | 1.1546E−03 |
| 279 | 1.2745E−03 |
| 280 | 1.1676E−03 |
| 281 | 1.2970E−03 |
| 282 | 1.2720E−03 |
| 283 | 1.3241E−03 |
| 284 | 1.3617E−03 |
| 285 | 1.3703E−03 |
| 286 | 1.4464E−03 |
| 287 | 1.3922E−03 |
| 288 | 1.5020E−03 |
| 289 | 1.4380E−03 |
| 290 | 1.4995E−03 |
| 291 | 1.4788E−03 |

TABLE 4-continued

Recorded absorbance values for CO and $H_2O$ monitoring referenced to spectrum in FIG. 11. Dispersion value for each channel is $2.58 \times 10^{-3}$ cm$^{-1}$.

| Channel # | Absorbance |
|---|---|
| 292 | 1.4919E−03 |
| 293 | 1.5484E−03 |
| 294 | 1.4794E−03 |
| 295 | 1.5743E−03 |
| 296 | 1.4764E−03 |
| 297 | 1.5229E−03 |
| 298 | 1.4395E−03 |
| 299 | 1.4667E−03 |
| 300 | 1.4362E−03 |
| 301 | 1.3864E−03 |
| 302 | 1.4615E−03 |
| 303 | 1.3444E−03 |
| 304 | 1.4194E−03 |
| 305 | 1.2928E−03 |
| 306 | 1.2957E−03 |
| 307 | 1.2172E−03 |
| 308 | 1.1961E−03 |
| 309 | 1.2276E−03 |
| 310 | 1.1251E−03 |
| 311 | 1.2234E−03 |
| 312 | 1.1114E−03 |
| 313 | 1.1475E−03 |
| 314 | 1.0785E−03 |
| 315 | 1.0191E−03 |
| 316 | 1.0217E−03 |
| 317 | 9.1945E−04 |
| 318 | 9.7901E−04 |
| 319 | 8.7208E−04 |
| 320 | 8.9824E−04 |
| 321 | 8.1039E−04 |
| 322 | 7.8902E−04 |
| 323 | 7.7233E−04 |
| 324 | 6.5146E−04 |
| 325 | 6.8682E−04 |
| 326 | 5.6608E−04 |
| 327 | 6.5334E−04 |
| 328 | 5.4678E−04 |
| 329 | 5.8193E−04 |
| 330 | 5.4621E−04 |
| 331 | 4.7277E−04 |
| 332 | 5.1247E−04 |
| 333 | 3.8253E−04 |
| 334 | 4.4564E−04 |
| 335 | 3.5812E−04 |
| 336 | 3.9758E−04 |
| 337 | 3.7587E−04 |
| 338 | 3.2595E−04 |
| 339 | 3.9812E−04 |
| 340 | 2.6365E−04 |
| 341 | 3.5913E−04 |
| 342 | 2.4816E−04 |
| 343 | 2.5911E−04 |
| 344 | 2.9343E−04 |
| 345 | 2.7617E−04 |
| 346 | 3.6663E−04 |
| 347 | 2.3685E−04 |
| 348 | 3.3183E−04 |
| 349 | 2.3953E−04 |
| 350 | 2.7353E−04 |
| 351 | 2.6539E−04 |
| 352 | 2.3384E−04 |
| 353 | 3.4718E−04 |
| 354 | 2.1273E−04 |
| 355 | 3.2123E−04 |
| 356 | 2.4748E−04 |
| 357 | 2.6712E−04 |
| 358 | 2.9603E−04 |
| 359 | 2.5023E−04 |
| 360 | 3.6773E−04 |
| 361 | 2.8448E−04 |
| 362 | 4.0186E−04 |
| 363 | 3.6052E−04 |
| 364 | 4.0781E−04 |
| 365 | 4.2704E−04 |
| 366 | 4.0423E−04 |
| 367 | 5.1670E−04 |
| 368 | 4.1914E−04 |
| 369 | 5.4546E−04 |
| 370 | 4.9913E−04 |
| 371 | 4.9008E−04 |
| 372 | 5.0431E−04 |
| 373 | 4.4861E−04 |
| 374 | 5.3729E−04 |
| 375 | 3.8373E−04 |
| 376 | 4.8155E−04 |
| 377 | 4.0247E−04 |
| 378 | 3.7924E−04 |
| 379 | 3.7920E−04 |
| 380 | 2.5380E−04 |
| 381 | 3.1865E−04 |
| 382 | 1.8406E−04 |
| 383 | 2.5340E−04 |
| 384 | 1.9759E−04 |
| 385 | 1.6958E−04 |
| 386 | 1.9705E−04 |
| 387 | 1.0422E−04 |
| 388 | 1.7783E−04 |
| 389 | 5.7294E−05 |
| 390 | 1.0763E−04 |
| 391 | 7.9453E−05 |
| 392 | 2.3581E−05 |
| 393 | 1.2911E−04 |
| 394 | −2.8256E−05 |
| 395 | 7.2472E−05 |
| 396 | −2.0368E−05 |
| 397 | −7.2734E−06 |
| 398 | 1.9575E−05 |
| 399 | −6.8640E−05 |
| 400 | 2.7098E−05 |
| 401 | −7.9558E−05 |
| 402 | −1.1540E−05 |
| 403 | −4.9291E−05 |
| 404 | −4.5727E−05 |
| 405 | 1.2920E−05 |
| 406 | −1.0755E−04 |
| 407 | 2.9012E−05 |
| 408 | −2.7308E−05 |
| 409 | −5.6117E−06 |
| 410 | 2.2753E−06 |
| 411 | −5.4111E−05 |
| 412 | 4.5417E−05 |
| 413 | −5.6893E−05 |
| 414 | 6.0828E−05 |
| 415 | 4.2674E−06 |
| 416 | −6.4615E−06 |
| 417 | 5.6088E−05 |
| 418 | −3.7183E−05 |
| 419 | 9.3948E−05 |
| 420 | 9.7324E−06 |
| 421 | 7.2048E−05 |
| 422 | 5.1128E−06 |
| 423 | 3.1553E−06 |
| 424 | −5.7451E−05 |
| 425 | 5.4995E−05 |
| 426 | −5.1295E−05 |
| 427 | 5.2667E−05 |
| 428 | 3.4742E−05 |
| 429 | 7.9860E−05 |
| 430 | 1.6699E−05 |
| 431 | 5.6749E−05 |
| 432 | 1.8161E−04 |
| 433 | 1.1344E−04 |
| 434 | −5.9261E−05 |
| 435 | −5.5664E−05 |
| 436 | 1.8464E−05 |
| 437 | −8.7975E−05 |

TABLE 4-continued

Recorded absorbance values for CO and H$_2$O monitoring referenced to spectrum in FIG. 11. Dispersion value for each channel is 2.58 ×10$^{-3}$ cm$^{-1}$.

| Channel # | Absorbance |
| --- | --- |
| 438 | 3.4540E–05 |
| 439 | 2.9952E–06 |
| 440 | 5.5075E–05 |
| 441 | 1.2036E–04 |
| 442 | 6.6895E–05 |
| 443 | 1.6734E–04 |
| 444 | 7.4437E–05 |

What is claimed is:

1. An apparatus for simultaneous detection of X gas species through laser radiation attenuation techniques, where at least one of the X gas species has a spectral absorption band whose wavelength is shorter than the cutoff wavelength for the other spectral absorption band, the apparatus comprising:
 a) N laser sources, wherein each of the N laser sources is adapted to operate at a wavelength $\lambda_N$ in a spectral absorption band separated by the cutoff wavelength for single mode transmission, each laser source corresponding to a spectral region for detecting a gas species;
 b) each of the N laser sources adapted to transmit radiation through an optical fiber constructed and arranged to provide single-mode transmission with minimal power loss to a beam splitter[BV1], said beam splitter sending a first portion of each of the N laser's radiation to a balanced ratiometric detector, and a second portion to a compound ferrule;
 c) the compound ferrule constructed and arranged so that each single-mode optical fiber terminating therein is held at a separation distance substantially less than a focal length of a collimating optical component to which the N beams are directed by the compound ferrule, the collimating optical component adapted to route N collimated laser beams through a process containing N gas species to be detected; and
 d) means for receiving and detecting nonabsorbed radiation from each laser and creating N outputs for each laser wavelength $\lambda_N$.

2. The apparatus of claim 1 wherein each of said N laser sources transmits through a dedicated corresponding single-mode optical fiber to said compound ferrule.

3. The apparatus of claim 1 wherein said compound ferrule is positioned within said beam launch module.

4. The apparatus of claim 1 wherein said compound ferrule allows said N laser sources to radiate onto means for collimating said N laser radiation beams and directing said collimated beams through a gas containing said N species to be detected.

5. The apparatus of claim 4 wherein said means for collimating is an off-axis parabolic mirror.

6. The apparatus of claim 4 further comprising a multi-chromic mirror having reflectance only for narrow bandpasses around said $8_N$ wavelengths, said multi-chromic mirror directing nonabsorbed radiation onto a second off-axis parabolic mirror, then through an iris, and then to a photodetector having a spectral response bandwidth encompassing $\lambda_n$ wavelengths, the photodetector producing an output for each $\lambda_N$ wavelength.

7. The apparatus of claim 5 wherein said N lasers are launched such that each beam is spatially separated from the other beams.

8. The apparatus of claim 7 wherein said gas being measured is bound by inlet and outlet windows coated on a portion thereof with antireflection coatings specific to each of said $\lambda_N$ wavelengths.

9. The apparatus of claim 8 wherein the receiving module includes N mirrors each having a narrow bandpass reflectance specific to each $\lambda_N$ wavelength and letting all other wavelengths pass through.

10. The apparatus of claim 9 wherein each N mirror has a corresponding off-axis parabolic mirror, an iris, and a detector.

11. The apparatus of claim 5 wherein said off-axis parabolic mirror directs said N through the gas and hence onto a grating.

12. The apparatus of claim 9 wherein each N mirror has a corresponding off-axis parabolic mirror, an iris, and a detector, each detector optically connected to a balanced ratiometric detector.

13. The apparatus of claim 12 wherein beams from said grating are reflected by and forwarded by N spherical mirrors, to respective iris and detectors.

14. A method for simultaneous detection of N gas species through laser radiation attenuation techniques comprising:
 (a) launching N laser wavelengths from N laser sources, wherein each of the N laser sources operates at a wavelength $\lambda_N$ in a spectral absorption band, the wavelength $\lambda_N$ being separated by a cutoff wavelength for single mode transmission, and each laser source corresponding to a gas species;
 (b) transmitting radiation from each of the N laser sources through an optical fiber, each optical fiber being constructed and arranged to provide single-mode transmission with minimal power loss to a compound ferrule;
 (c) separating each single-mode optical fiber using the compound ferrule thus creating N collimated laser beams;
 (d) routing the N collimated laser beams through a medium having N species to be detected; and
 (e) receiving and detecting radiation corresponding to the N gas species to be detected.

15. The method of claim 14 further comprising transmitting each of said N lasers through a dedicated corresponding single-mode optical fiber to said compound ferrule.

16. The method of claim 14 further comprising positioning said compound ferrule within said beam launch module.

17. The method of claim 14, further comprising routing said N laser beams using said ferrule onto means for collimating said N laser radiation beams and directing said collimated beams through a gas containing said N species or N spectral features to be detected.

18. The method of claim 17, comprising collimating said N beams using an off-axis parabolic mirror.

19. The method of claim 18, further comprising routing the N beams using a multi-chromic mirror having reflectance for narrow bandpasses around said $\lambda_N$ wavelengths, said multi-chromic mirror directing nonabsorbed radiation onto a second off-axis parabolic mirror, where it is then directed through an iris, and subsequently to a photodetector having a spectral response bandwidth encompassing $\lambda_n$ wavelengths, the photodetector producing an output for each $\lambda_N$ wavelength.

20. The method of claim 14, further comprising producing an output, and digitizing and analyzing said output by a means for data acquisition.

21. The method of claim 18, further comprising launching said N lasers and spatially separating each beam from the other beams.

22. The method of claim 21, further comprising routing said N beams through the gas, the gas being bound by inlet and outlet windows coated on a portion thereof with anti-reflection coatings specific to each of said $\lambda_N$ wavelengths.

23. The method of claim 22, further comprising routing the N beams to a receiving module including N mirrors each having a narrow bandpass reflectance specific to each $\lambda_N$ wavelength and letting all other wavelengths pass through.

24. The method of claim 23, further comprising routing each beam from said N mirrors to a corresponding off-axis parabolic mirror, an iris, and a detector.

25. The method of claim 18, further comprising routing said N beams from said off-axis parabolic mirror through the gas and hence onto a grating.

26. The method of claim 23, further comprising routing each N beam from said N mirrors to a corresponding off-axis parabolic mirror, an iris, and a detector.

27. The method of claim 26, further comprising routing said N beams from said grating to N spherical mirrors, and then from said N spherical mirrors to respective irises and detectors.

28. An apparatus for simultaneous detection of N gas species through laser radiation attenuation techniques comprising:
(a) N laser sources, each of the N laser sources being adapted to operate at a wavelength $\lambda_N$ in a spectral absorption band separated by the cutoff wavelength for single mode transmission, each laser source corresponding to a gas species;
(b) each of the N laser sources adapted to transmit radiation through an optical fiber constructed and arranged to provide single-mode transmission with minimal power loss to N achromat lenses adapted to create N collimated laser beams;
(c) means for launching the N collimated laser beams into a medium containing the N gas species to be detected; and
(d) means for receiving and detecting portions of the N collimated laser beams.

29. The apparatus of claim 28 wherein the means for receiving and detecting portions of the N collimated laser beams comprises a prism, an achromat lens, and a spherical lens combination.

30. The apparatus of claim 28 wherein each of the N laser sources is adapted to transmit radiation through N dedicated optical fibers, each of the N optical fibers having single-mode optical fiber characteristics sufficient to insure single-mode transmission with minimal power loss.

31. The apparatus of claim 28 wherein the means for launching is selected from the group consisting of a dichroic beam combiner and a system of mirrors.

32. A method for simultaneous detection of N gas species through laser radiation attenuation techniques comprising:
(a) providing N laser sources, wherein each of the N laser sources is adapted to operate at a wavelength $\lambda_N$ in a spectral absorption band separated by the cutoff wavelength far single mode transmission, each laser source corresponding to a gas species;
(b) transmitting each of the wavelengths $\lambda_N$ through an optical fiber, each optical fiber having single-mode optical fiber characteristics sufficient to insure single-mode transmission with minimal power loss to N achromat lenses, each achromat lens having a proper wavelength-specific anti-reflective coating, the N achromat lenses adapted to create N collimated laser beams;
(c) launching the N collimated laser beams into the process containing the N gas species to be detected; and
(d) receiving and detecting nonabsorbed portions of the N collimated laser beams.

33. The apparatus of claim 28, wherein:
the means for receiving and detecting portions of the N collimated laser beams comprises a prism, a convex lens paired with a concave lens, a spherical mirror, and N detectors;
the prism, the paired convex and concave lenses, the spherical mirror and the N detectors being configured and adapted to allow the N collimated laser beams to pass through the prism to the paired convex and concave lenses where the N collimated laser beams are decollimated and focused towards the spherical mirror where the N decollimated laser beams are reflected thereby onto N detectors; and
each of the N detectors receives and detects radiation corresponding to a different wavelength $\lambda_N$.

34. The method of claim 32, wherein the receiving and detecting step comprises the steps of:
allowing the N collimated laser beams to pass through the prism to paired convex and concave lenses;
allowing the N collimated laser beams to be decollimated by the paired convex and concave lenses and focused thereby towards a spherical mirror; and
allowing the spherical mirror to reflect the focused N decollimated laser beams onto N detectors where radiation associated with the nonabsorbed portions is detected, each of the N detectors being associated with a different wavelength $\lambda_N$.

* * * * *

UNITED STATES PATENT AND TRADEMARK OFFICE
CERTIFICATE OF CORRECTION

| | | |
|---|---|---|
| PATENT NO. | : 7,005,645 B2 | Page 1 of 1 |
| APPLICATION NO. | : 10/294061 | |
| DATED | : February 28, 2006 | |
| INVENTOR(S) | : William A. Von Drasek et al. | |

It is certified that error appears in the above-identified patent and that said Letters Patent is hereby corrected as shown below:

In Column 35, line 32, delete "[BV1]".
In Column 35, line 62, replace "$8_N$" with --$\lambda n$--.

Col. 1 line 4 Insert as new paragraph [0001]: --This invention was made with government support under Contract No. DE-FC36-00CH11030 awarded by the Department of Energy. The government has certain rights in this invention.--

Signed and Sealed this

Fifth Day of September, 2006

JON W. DUDAS
*Director of the United States Patent and Trademark Office*